United States Patent [19]

Karanewsky et al.

[11] 4,452,790

[45] Jun. 5, 1984

[54] PHOSPHONYL HYDROXYACYL AMINO ACID DERIVATIVES AS ANTIHYPERTENSIVES

[75] Inventors: Donald S. Karanewsky, Princeton Junction; Edward W. Petrillo, Jr., Pennington, both of N.J.

[73] Assignee: E. R. Squibb & Sons, Inc., Princeton, N.J.

[21] Appl. No.: 391,884

[22] Filed: Jun. 23, 1982

[51] Int. Cl.³ .................... A61K 31/675; C07F 9/65
[52] U.S. Cl. .................... 424/200; 546/22; 546/23; 548/112; 548/119; 548/409; 548/413; 548/414
[58] Field of Search .......... 548/409, 413, 414, 112, 548/119; 546/22, 23; 424/200

[56] References Cited

U.S. PATENT DOCUMENTS

| 4,053,651 | 10/1977 | Ondetti et al. | 424/319 |
|---|---|---|---|
| 4,105,776 | 8/1978 | Ondetti et al. | 424/274 |
| 4,129,566 | 12/1978 | Ondetti et al. | 546/326 |
| 4,151,172 | 4/1979 | Ondetti et al. | 548/413 |
| 4,154,935 | 5/1979 | Ondetti et al. | 546/189 |
| 4,168,267 | 9/1979 | Petrillo | 548/413 |
| 4,192,878 | 3/1980 | Ondetti | 424/270 |
| 4,199,512 | 4/1980 | Ondetti et al. | 548/455 |
| 4,217,359 | 8/1979 | Krapcho | 424/274 |
| 4,234,489 | 11/1980 | Ondetti et al. | 424/274 X |
| 4,256,761 | 3/1981 | Suh et al. | 424/282 |
| 4,296,033 | 10/1981 | Petrillo et al. | 424/274 X |
| 4,296,113 | 10/1981 | Ondetti | 424/246 |
| 4,303,583 | 12/1981 | Kim et al. | 424/200 X |
| 4,316,896 | 2/1982 | Thorsett et al. | 424/200 |
| 4,337,201 | 6/1982 | Petrillo, Jr. | 548/413 |
| 4,374,131 | 2/1983 | Petrillo, Jr. | 424/200 |
| 4,379,146 | 4/1983 | Greenlee et al. | 424/177 |
| 4,381,297 | 4/1983 | Karanewsky et al. | 424/200 |

FOREIGN PATENT DOCUMENTS

| 868532 | 10/1978 | Belgium . | |
|---|---|---|---|
| 9183 | 4/1980 | European Pat. Off. | 424/200 |
| 2027025 | 2/1980 | United Kingdom . | |
| 2028327 | 3/1980 | United Kingdom . | |
| 2039478 | 8/1980 | United Kingdom . | |

OTHER PUBLICATIONS

Galardy, "Inhibition of Angiotensin . . . " Biochem. Biophs. Res. Comm., 1980, vol. 97, pp. 94-99.
Mauger, "Analogs and Homologs of Proline . . . ", Chem. Review, vol. 66, pp. 47-86 (1966).
Thorsett et al., "Phosphorus Containing Inhibitors . . . ", 182 National Meeting, ACS, New York, Aug. 1981, MEDI-7, Proc. Natl. Acad. Sci., USA, vol. 79, pp. 2176-2180 (04/82).

Primary Examiner—Donald G. Daus
Assistant Examiner—Diana G. Rivers
Attorney, Agent, or Firm—Lawrence S. Levinson; Burton Rodney

[57] ABSTRACT

Phosphonyl hydroxyacyl amino acids of the formula

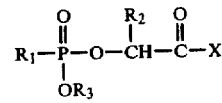

wherein X is a substituted or unsubstituted imino or amino acid or ester. These compounds possess angiotensin converting enzyme activity and are thus useful as hypotensive agents.

21 Claims, No Drawings

PHOSPHONYL HYDROXYACYL AMINO ACID DERIVATIVES AS ANTIHYPERTENSIVES

BACKGROUND OF THE INVENTION

Thorsett, et al. in U.S. Pat. No. 4,316,896 disclose phosphoryl derivatives of aminoacids including proline. These compounds are disclosed as being hypotensive agents due to their angiotensin converting enzyme inhibition activity.

Petrillo in U.S. Pat. No. 4,168,267 discloses that various phosphinylalkanoyl substituted prolines are useful as hypotensive agents due to their ability to inhibit the angiotensin converting enzyme.

Ondetti et al. in U.S. Pat. No. 4,151,172 disclose that various phosphonoacyl prolines are useful as hypotensive agents due to their ability to inhibit the angiotensin converting enzyme.

Mercaptoacyl derivatives of proline and substituted prolines are known to be useful hypotensive agents due to their angiotensin converting enzyme inhibition activity. Ondetti et al. in U.S. Pat. No. 4,105,776 disclose such compounds wherein the proline ring is unsubstituted or substituted by an alkyl or hydroxy group. Ondetti et al. in U.S. Pat. No. 4,154,935 disclose such compounds wherein the proline ring is substituted with one or more halogens. Ondetti et al. in U.K. Patent Application No. 2,028,327 disclose such compounds wherein the proline ring is substituted by various ethers and thioethers. Krapcho in U.S. Pat. No. 4,217,359 discloses such compounds wherein the proline ring has a carbamoyloxy substituent. Krapcho in U.K. Patent Application No. 2,039,478 discloses compounds wherein the proline ring has a diether, dithioether, ketal or thioketal substituent in the 4-position. Krapcho in U.S. Pat. No. 4,316,905 discloses such compounds wherein the proline ring has a cycloalkyl, phenyl, or phenyl-lower alkylene substituent. Ondetti et al. in U.S. Pat. No. 4,234,489 disclose such compounds wherein the proline has a keto substituent in the 5-position. Krapcho et al. in U.S. Pat. No. 4,310,461 disclose such compounds wherein the proline has an imido, amido, or amino substituent in the 4-position. Iwao et al. in U.K. Patent Application No. 2,027,025 disclose such compounds wherein the proline has an aromatic substituent in the 5-position. Ondetti et al. in U.S. Pat. Nos. 4,053,651 and 4,199,512 disclose that mercaptoacyl derivatives of various aminoacids other than proline are also useful angiotensin converting enzyme inhibitors.

Karanewsky and Petrillo in U.S. Ser. No. 289,671 disclose phosphonamidate substituted amine or imino acids.

Mercaptoacyl derivatives of 3,4-dehydroproline are disclosed as angiotensin converting enzyme inhibitors by Ondetti in U.S. Pat. No. 4,129,566. Mercaptoacyl derivatives of thiazolidinecarboxylic acid and substituted thiazolidinecarboxylic acid are disclosed as angiotensin converting enzyme inhibitors by Ondetti in U.S. Pat. No. 4,192,878 and by Yoshitomo Pharmaceutical Ind. in Belgian Patent No. 868,532.

SUMMARY OF THE INVENTION

This invention is directed to new phosphonate substituted amino or imino acids of formula I and salts thereof

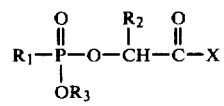

X is an imino or amino acid of the formula

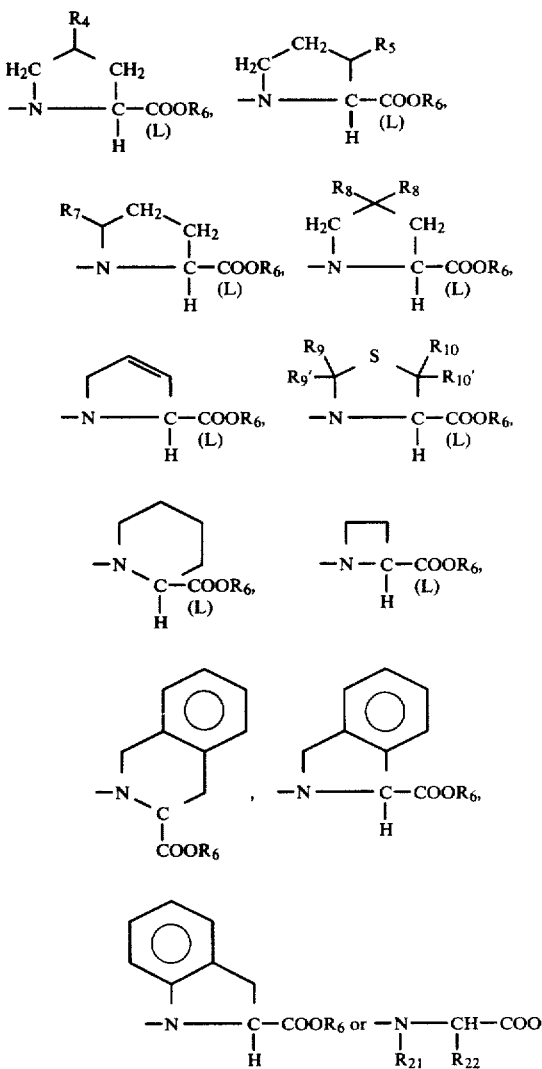

$R_4$ is hydrogen, lower alkyl, halogen, keto, hydroxy,

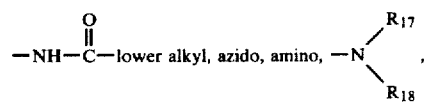

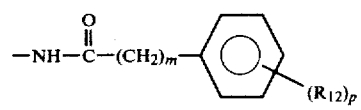

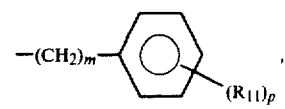

-continued

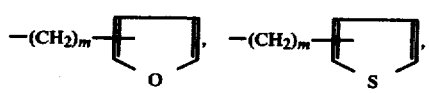

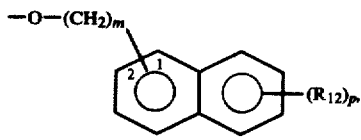

—S—lower alkyl,

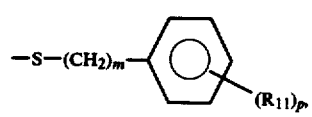

a 1- or 2-naphthyl of the formula

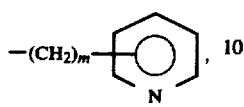

or a 1- or 2-naphthylthio of the formula

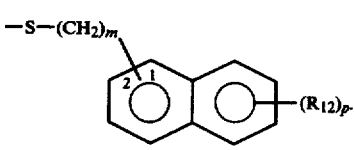

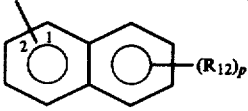

R₇ is keto or

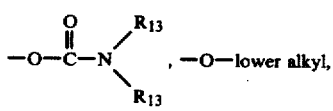

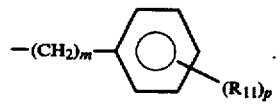

Each $R_8$ is independently halogen or —Y—$R_{14}$.

$R_9$, $R_9'$, $R_{10}$ and $R_{10}'$ are independently selected from hydrogen and lower alkyl or $R_9'$, $R_{10}$ and $R_{10}'$ are hydrogen and $R_9$ is

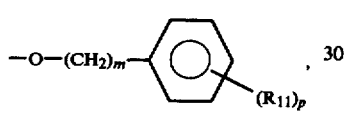

a 1- or 2-naphthyloxy of the formula

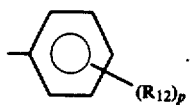

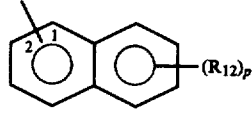

$R_{11}$ is hydrogen, lower alkyl of 1 to 4 carbons, lower alkoxy of 1 to 4 carbons, lower alkylthio of 1 to 4 carbons, chloro, bromo, fluoro, trifluoromethyl, hydroxy, phenyl, phenoxy, phenylthio, or phenylmethyl.

$R_{12}$ is hydrogen, lower alkyl of 1 to 4 carbons, lower alkoxy of 1 to 4 carbons, lower alkylthio of 1 to 4 carbons, chloro, bromo, fluoro, trifluoromethyl, or hydroxy.

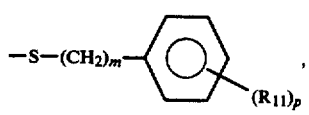

or a 1- or 2-naphthylthio of the formula

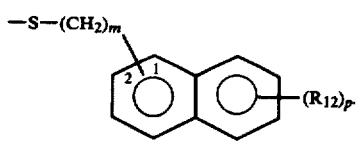

$R_5$ is keto, halogen, m is zero, one, two or three.

p is one, two or three provided that p is more than one only if $R_{11}$ or $R_{12}$ is hydrogen, methyl, methoxy, chloro, or fluoro.

$R_{13}$ is hydrogen or lower alkyl of 1 to 4 carbons.

Y is oxygen or sulfur.

$R_{14}$ is lower alkyl of 1 to 4 carbons,

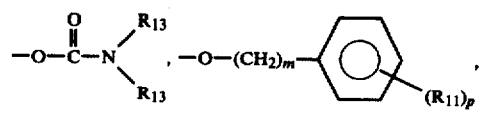

—O—lower alkyl, a 1- or 2-naphthyloxy of the formula

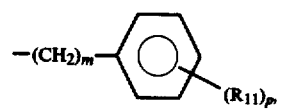

or the $R_{14}$ groups join to complete an unsubstituted 5- or 6-membered ring or said ring in which one or more of the carbons has a lower alkyl of 1 to 4 carbons or a di(lower alkyl of 1 to 4 carbons) substituent.

$R_{21}$ is hydrogen, lower alkyl, cycloalkyl, phenyl, or

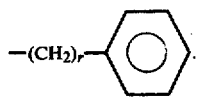

$R_{22}$ is hydrogen, lower alkyl,

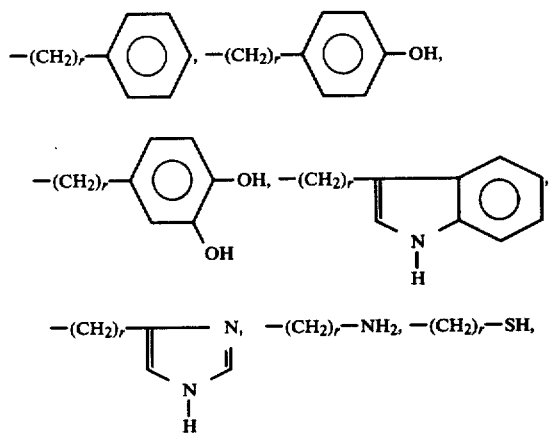

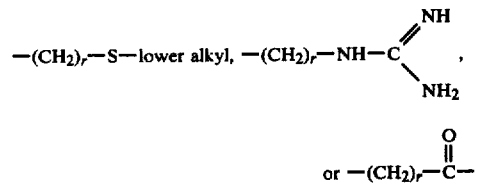

or $-(CH_2)_r-\overset{O}{\underset{\|}{C}}-NH_2$.

r is an integer from 1 to 4.
$R_1$ is alkyl of 1 to 10 carbons, aminoalkyl, haloalkyl,

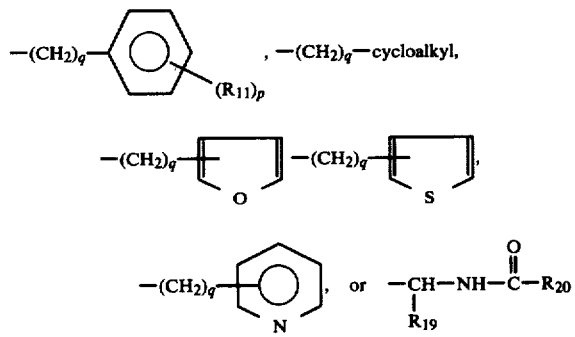

wherein q is zero or an integer from 1 to 7 and $R_{12}$ and p are as defined above.

$R_{19}$ and $R_{20}$ are independently selected from hydrogen, lower alkyl, halo substituted lower alkyl,

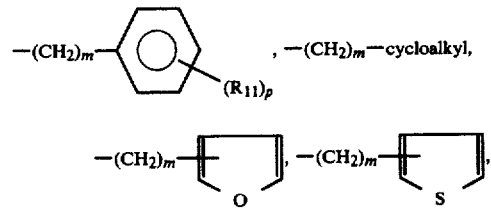

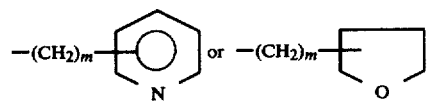

wherein m, $R_{11}$, and p are as defined above.

$R_2$ is hydrogen, lower alkyl, halo substituted lower alkyl,

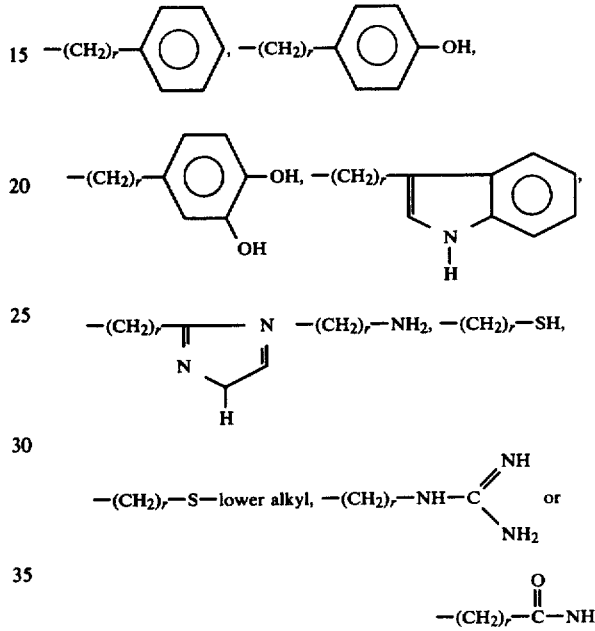

wherein r is as defined above.

$R_3$ and $R_6$ are independently selected from hydrogen, lower alkyl, benzyl, alkali metal such as Li, Na or K, benzhydryl, or

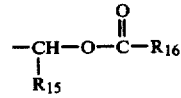

wherein $R_{15}$ is hydrogen, lower alkyl, cycloalkyl, or phenyl, and $R_{16}$ is hydrogen, lower alkyl, lower alkoxy, phenyl, or $R_{15}$ and $R_{16}$ taken together are $-(CH_2)_2-$, $-(CH_2)_3-$, $-CH=CH-$, or

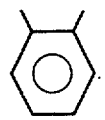

$R_{17}$ is lower alkyl, benzyl, or phenethyl.
$R_{18}$ is hydrogen, lower alkyl, benzyl or phenethyl.

DETAILED DESCRIPTION OF THE INVENTION

This invention in its broadest aspects relates to the phosphonate substituted imino or amino acid compounds of formula I above, to compositions containing such compounds and to the method of using such compounds as anti-hypertensive agents.

The term alkyl used in defining $R_1$ refers to straight or branched chain hydrocarbon radicals having up to ten carbons, for example, methyl, ethyl, propyl, isopropyl, butyl, isobutyl, t-butyl, pentyl, isopentyl, heptyl, octyl, decyl, etc. The term lower alkyl used in defining various symbols refers to straight or branched chain radicals having up to seven carbons. The preferred lower alkyl groups are up to four carbons with methyl and ethyl most preferred. Similarly the terms lower alkoxy and lower alkylthio refer to such lower alkyl groups attached to an oxygen or sulfur.

The term cycloalkyl refers to saturated rings of 3 to 7 carbon atoms with cyclopentyl and cyclohexyl being most preferred.

The term halo refers to Cl, Br and F. The term halo substituted lower alkyl refers to such lower alkyl groups described above in which one or more hydrogens have been replaced by chloro, bromo or fluoro groups such as trifluoromethyl, which is preferred, pentafluoroethyl, 2,2,2-trichloroethyl, chloromethyl, bromomethyl, etc. Similarly, the term amino substituted lower alkyl refers to lower alkyl groups in which one or more hydrogens have been replaced by $-NH_2$, i.e., aminomethyl, 2-aminoethyl, etc. The symbols

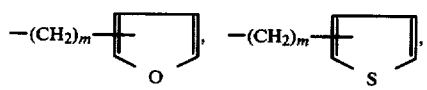

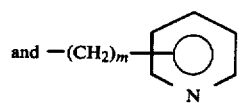

represent that the alkylene bridge is attached to an available carbon atom.

The compounds of formula I wherein $R_1$ is other than

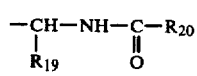

are prepared according to the following procedures. A phosphonic acid of formula II

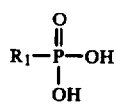
II wherein $R_1$ is as defined above is treated with a chlorinating agent such as phosphorus pentachloride in the presence of an inert organic solvent such as benzene to form a compound of the formula

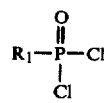
III which is reacted with a lactate of the formula

IV in the presence of an organic base such as triethylamine followed by an alcohol $R_3OH$ (where $R_3$ is lower alkyl, benzyl, or benzhydryl) to form a compound of the formula

V

The formula V compound is then treated with strong base such as sodium hydroxide or lithium hydroxide in a mixture of water and an organic solvent such as dioxane to form the corresponding acid

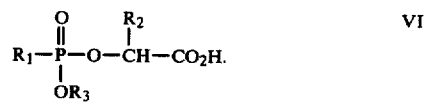
VI

The acid VI or its activated form is then coupled with an imino or amino acid or ester of the formula

H—X.    VII

The term activated form refers to the conversion of the acid to a mixed anhydride, symmetrical anhydride, acid chloride, or activated ester, see Methoden der Organischen Chemie (Houben-Weyl), Vol. XV, part II, page 1 et seq. (1974) for a review of the methods of acylation. Preferably the reaction is performed in the presence of a coupling agent such as 1,1-carbonyldiimidazole, thionyl chloride, or dicyclohexylcarbodiimide.

In the above reaction if $R_2$ is

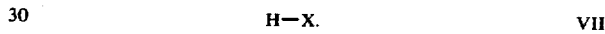

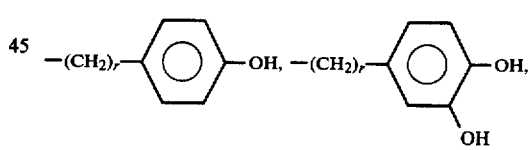

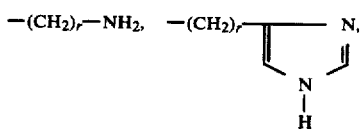

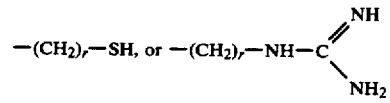

then the hydroxyl, amino, imidazolyl, mercaptan, or guanidinyl function should be protected during the coupling reaction. Suitable protecting groups include benzyloxycarbonyl, t-butoxycarbonyl, benzyl, benzhydryl, trityl, etc., and nitro in the case of guanidinyl. The protecting group is removed by hydrogenation, treatment with acid, or other known methods following completion of the reaction.

Similarly, if in the above reaction R₁=aminoalkyl, then the amino group should be similarly protected, preferably by phthalidyl. The protecting group is removed by treatment with hydrazine following completion of the reaction.

The products of formula I wherein either or both of R₃ and R₆ are lower alkyl, benzyl, or benzhydryl can be hydrogenated, for example, by treating with hydrogen in the presence of a palladium on carbon catalyst or chemically treated such as with sodium hydroxide in aqueous dioxane or with trimethylsilylbromide in dichloromethane to yield the products of formula I wherein R₃ and R₆ are hydrogen.

The ester products of formula I wherein R₆ is

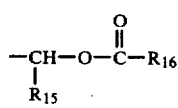

may be obtained by employing the imino or amino acid of formula V in the above reactions with the ester group already in place. Such ester reactants can be prepared by treating peptide, imino, or amino acids with an acid chloride such as

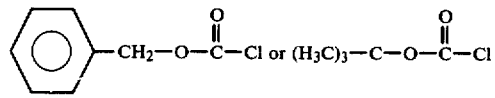

so as to protect the N-atom. The protected acid compound is then reacted in the presence of base with a compound of the formula

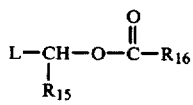    VIII wherein L is a leaving group such as chlorine, bromine, tolylsulfonyloxy, etc., followed by removal of the N-protecting group such as by treatment with acid or hydrogenation.

The ester products of formula I wherein R₆ is

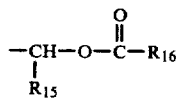

can also be obtained by treating the product of formula I wherein R₆ is hydrogen with a molar equivalent of the compound of formula VIII. The diester products wherein R₃ and R₆ are the same and are

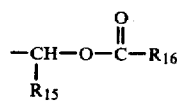

can be obtained by treating the product of formula I wherein R₃ and R₆ are both hydrogen or an alkali metal salt with two or more equivalents of the compound of formula VIII.

The ester products of formula I wherein R₃ is

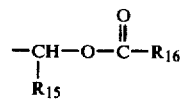

can be obtained by treating the product of formula I wherein R₃ is hydrogen or an alkali metal salt and R₆ is benzyl or benzhydryl with the compound of formula VIII in the presence of base. Removal of the R₆ ester group such as by hydrogenation yields the products of formula I wherein R₃ is

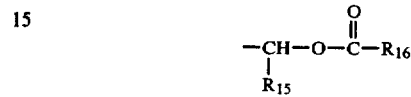

and R₆ is hydrogen.

The products of formula I wherein R₄ is amino may be obtained by reducing the corresponding products of formula I wherein R₄ is azido.

The various imino and amino acids and esters of formula V are described in the literature and in the various patents and pending U.S. application referred to above. Various substituted prolines are also disclosed by Mauger et al., Chem. Review, Vol. 66, p. 47–86 (1966). When the amino or imino acid is known, it can be readily converted to the ester by conventional means. For example, the esters where R₆ is t-butyl can be obtained by treating the corresponding N-carbobenzyloxyimino acid with isobutylene under acidic conditions and then removing the N-carbobenzyloxy protecting group by catalytic hydrogenation and the esters wherein R₆ is benzyl can be obtained by treating the imino acid with benzyl alcohol and thionyl chloride.

As disclosed by Krapcho in U.S. Ser. No. 164,985, the substituted prolines wherein R₄ is

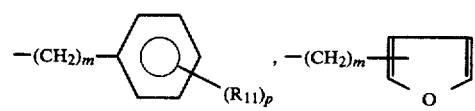

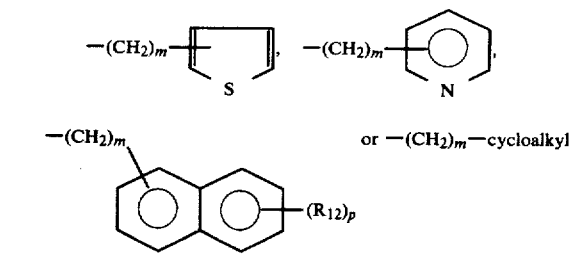

are prepared by reacting a 4-keto proline of the formula

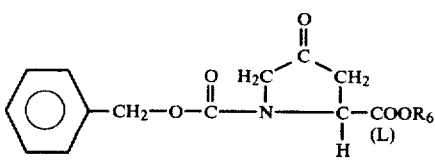    IX with a solution of the Grignard or lithium reagent $R_4$—Mg—halo or $R_4$—Li   X wherein $R_4$ is as defined above and halo is Br or Cl to yield

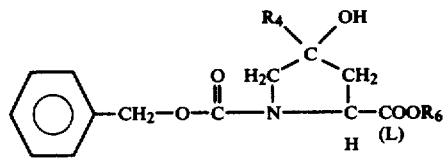

XI

This compound is treated with a dehydrating agent such as p-toluenesulfonic acid, sulfuric acid, potassium bisulfate, or trifluoroacetic acid to yield the 3,4-dehydro-4-substituted proline of the formula

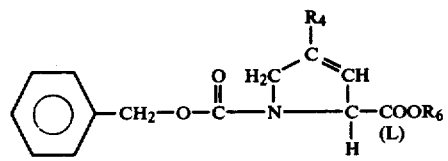

XII

Removal of the N-benzyloxycarbonyl protecting group and hydrogenation of the compound of formula XII yields the desired starting materials. The substituted proline wherein $R_4$ is cyclohexyl can be prepared by further hydrogenation of the 4-phenyl proline compound.

The substituted prolines wherein $R_4$ is the substituted amino group

may be prepared by reacting a 4-keto proline of formula IX with the amine

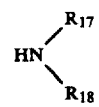

in the presence of hydrogen and catalyst or in the presence of sodium cyanotrihydridoborate.

The compounds of formula I wherein $R_1$ is

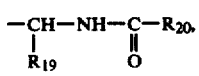

that is

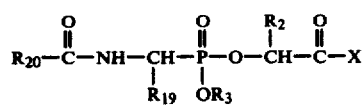

XIII may be prepared by reacting an aminophosphonic acid of the formula

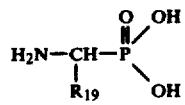

XIV with an acid chloride having the formula

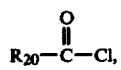

XV such as benzoyl chloride, in the presence of an inert organic solvent, such as dioxane and a weak organic base, such as triethylamine to yield

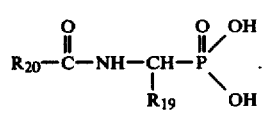

XVI

The formula XVI compound is then coupled with an imino or amino acid or ester of formula XVII

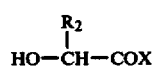

XVII in the presence of a coupling agent, such as dicyclohexylcarbodiimide as described above to form

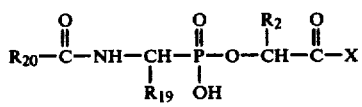

XVIII

Where X includes a protecting group, it may be removed by hydrogenation wherein the protecting group is phenylmethoxycarbonyl or by treatment with hydrazine where the protecting group is phthalidyl to yield the compounds of formula XIII.

The compounds of formula XVII may be prepared by coupling a hydroxy acid of formula XIX as the free acid or corresponding sodium salt

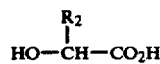

XIX with an imino or amino ester of formula VII preferably in the presence of a coupling agent such as diphenyl phosphorylazide.

Preferred compounds of this invention with respect to the amino or imino acid or ester part of the structure of formula I are those wherein:

$R_{21}$ is hydrogen, methyl, phenyl, cyclopentyl or cyclohexyl;

$R_{22}$ is hydrogen, lower alkyl of 1 to 4 carbons,

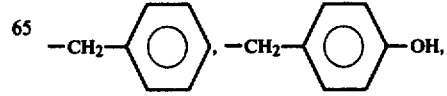

-continued

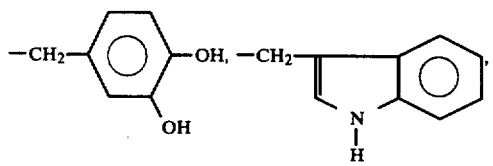

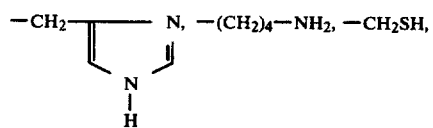

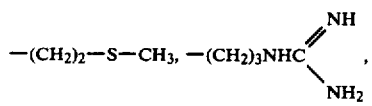

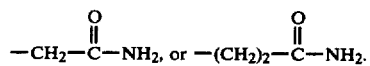

$R_6$ is hydrogen, an alkali metal salt, or

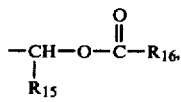

$R_{15}$ is hydrogen, methyl or isopropyl and $R_{16}$ is straight or branched chain lower alkyl of 1 to 4 carbons or phenyl.

$R_4$ is hydrogen.

$R_4$ is hydroxy.

$R_4$ is chloro or fluoro.

$R_4$ is lower alkyl of 1 to 4 carbons or cyclohexyl.

$R_4$ is amino.

$R_4$ is —O—lower alkyl wherein lower alkyl is straight or branched chain of 1 to 4 carbons.

$R_4$ is

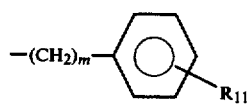

wherein m is zero, one or two, $R_{11}$ is hydrogen, methyl, methoxy, methylthio, chloro, bromo, fluoro, or hydroxy.

$R_4$ is

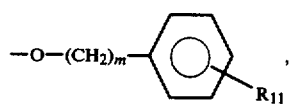

1-naphthyloxy, or 2-naphthyloxy wherein m is zero, one or two, and $R_{11}$ is hydrogen, methyl, methoxy, methylthio, chloro, bromo, fluoro, or hydroxy.

$R_4$ is —S—lower alkyl wherein lower alkyl is straight or branched chain of 1 to 4 carbons.

$R_4$ is

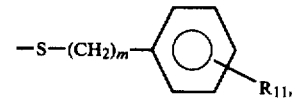

1-naphthylthio, or 2-naphthylthio wherein m is zero, one or two, and $R_{11}$ is hydrogen, methyl, methoxy, methylthio, chloro, bromo, fluoro, or hydroxy.

$R_5$ is —O—lower alkyl wherein lower alkyl is straight or branched chain of 1 to 4 carbons.

$R_5$ is

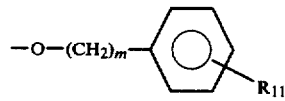

wherein m is zero, one or two, and $R_{11}$ is hydrogen, methyl, methoxy, methylthio, chloro, bromo, fluoro, or hydroxy.

$R_5$ is —S—lower alkyl wherein lower alkyl is straight or branched chain of 1 to 4 carbons.

$R_5$ is

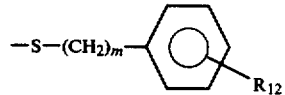

wherein m is zero, one or two, and $R_{12}$ is hydrogen, methyl, methoxy, methylthio, chloro, bromo, fluoro, or hydroxy.

$R_7$ is phenyl, 2-hydroxyphenyl, or 4-hydroxyphenyl.

Each $R_8$ is independently fluoro or chloro.

Each $R_8$ is independently —Y—$R_{14}$ wherein Y is O or S, $R_{14}$ is straight or branched chain alkyl of 1 to 4 carbons or the $R_{14}$ groups join to complete an unsubstituted 5- or 6-membered ring or said ring in which one or more of the carbons has a methyl or dimethyl substituent.

$R_9$, $R_9'$, $R_{10}$ and $R_{10}'$ are all hydrogen, or $R_9$ is phenyl, 2-hydroxyphenyl or 4-hydroxyphenyl and $R_9'$, $R_{10}$ and $R_{10}'$ are hydrogen.

Most preferred compounds of this invention with respect to the amino or imino acid or ester part of the structure of formula I are those wherein:

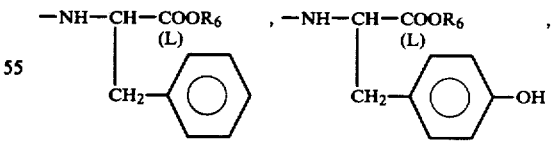

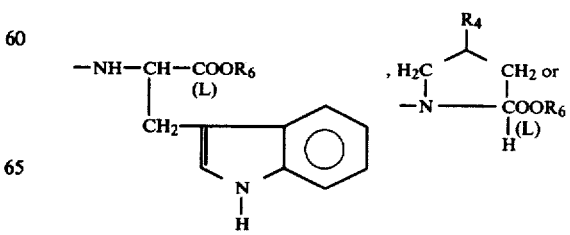

-continued

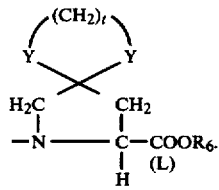

$R_6$ is hydrogen,

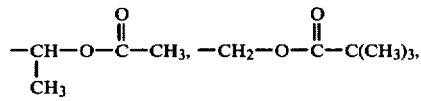

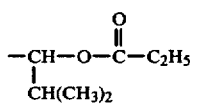

or an alkali metal salt.

$R_4$ is hydrogen.
$R_4$ is cyclohexyl.
$R_4$ is lower alkoxy of 1 to 4 carbons.
$R_4$ is

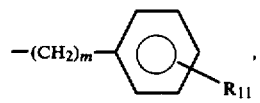

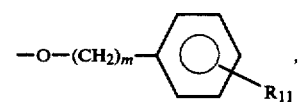

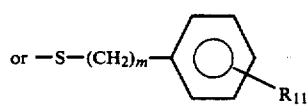

wherein m is zero, one, or two and $R_{11}$ is hydrogen, methyl, methoxy, methylthio, Cl, Br, F or hydroxy.

Y is oxygen or sulfur and t is two or three, especially wherein Y is sulfur and t is two.

Preferred compounds of this invention with respect to the phosphonyl sidechain of the structure of formula I are those wherein:

$R_2$ is hydrogen, lower alkyl of 1 to 4 carbons, $CF_3$, or amino substituted lower alkyl of 1 to 4 carbons, especially hydrogen, methyl or $-(CH_2)_4NH_2$.

$R_3$ is hydrogen, an alkali metal salt, lower alkyl of 1 to 4 carbons, or

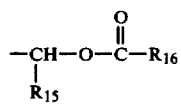

wherein $R_{15}$ is hydrogen, methyl or isopropyl and $R_{16}$ is straight or branched chain lower alkyl of 1 to 4 carbons or phenyl, especially hydrogen, alkali metal salt, ethyl,

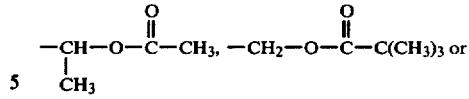

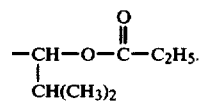

$R_1$ is alkyl of 1 to 10 carbons;

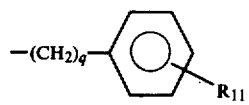

wherein q is zero or an integer from 1 to 4 and $R_{11}$ is hydrogen, methyl, methoxy, methylthio, chloro, bromo, fluoro, or hydroxy; $-(CH_2)_q-$ cycloalkyl wherein cycloalkyl is of 5 or 6 carbons and q is zero, one or two;

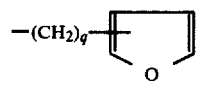

wherein q is zero or an integer from 1 to 4,

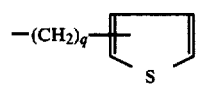

wherein q is zero or an integer from 1 to 4,

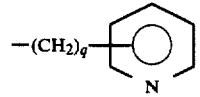

wherein q is zero or an integer from 1 to 4 or

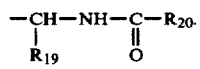

$R_{19}$ and $R_{20}$ are independently selected from lower alkyl of 1 to 4 carbons or

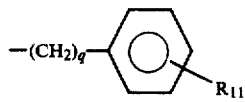

wherein q is zero or an integer from 1 to 4 and $R_{11}$ is hydrogen, methyl, methoxy, methylthio, chloro, bromo, fluoro, or hydroxy, especially wherein $R_{19}$ is phenylethyl and $R_{20}$ is phenyl.

The compounds of this invention wherein at least one of $R_3$ or $R_6$ is hydrogen, form basic salts with various inorganic and organic bases which are also within the scope of the invention. Such salts include ammonium salts, alkali metal salts like lithium, sodium and potassium salts (which are preferred), alkaline earth metal salts like calcium and magnesium salts, salts with organic bases, e.g., dicyclohexylamine salt, benzathine, N-methyl-D-glucamine, hydrabamine salts, salts with amino acids like arginine, lysine and the like. The nontoxic physiologically acceptable salts are preferred, although other salts are also useful, e.g., in isolating or purifying the product. The salts are formed using conventional techniques.

As shown above, the amino or imino acid or ester portion of the molecule of the products of formula I represented by X is in the L-configuration. Depending upon the definition of $R_2$ and $R_{19}$ other asymmetric center may be present in the phosphonyl sidechain. Thus, some of the compounds can accordingly exist in diastereoisomeric forms or in mixtures thereof. The above described processes can utilize racemates, enantiomers or diastereomers as starting materials. When diastereomeric products are prepared, they can be separated by conventional chromatographic or fractional crystallization methods.

The products of formula I wherein the imino acid ring is monosubstituted give rise to cis-trans isomerism. The configuration of the final product will depend upon the configuration of the $R_4$, $R_5$ and $R_7$ substituent in the starting material.

The compounds of formula I, and the physiologically acceptable salts thereof, are hypotensive agents. They inhibit the conversion of the decapeptide angiotensin I to angiotensin II and, therefore, are useful in reducing or relieving angiotensin related hypertension. The action of the enzyme renin on angiotensinogen, a pseudoglobulin in blood pressure, produces angiotensin I. Angiotensin I is converted by angiotensin converting enzyme (ACE) to angiotensin II. The latter is an active pressor substance which has been implicated as the causative agent in several forms of hypertension in various mammalian species, e.g., humans. The compounds of this invention intervene in the angiotensinogen→(renin)→angiotensin I→angiotensin II sequence by inhibiting angiotensin converting enzyme and reducing or eliminating the formation of the pressor substance angiotensin II. Thus by the administration of a composition containing one (or a combination) of the compounds of this invention, angiotensin dependent hypertension in a species of mammal (e.g., humans) suffering therefrom is alleviated. A single dose, or preferably two or four divided daily doses, provided on a basis of about 0.1 to 100 mg per kilogram of body weight per day is appropriate to reduce blood pressure. The substance is preferably administered orally, but parenteral routes such as the subcutaneous, intramuscular, intravenous or intraperitoneal routes can also be employed.

The compounds of this invention can also be formulated in combination with a diuretic for the treatment of hypertension. A combination product comprising a compound of this invention and a diuretic can be administered in an effective amount which comprises a total daily dosage of about 30 to 600 mg., preferably about 30 to 330 mg of a compound of this invention, and about 15 to 300 mg, preferably about 15 to 200 mg of the diuretic, to a mammalian species in need thereof. Exemplary of the diuretics contemplated for use in combination with a compound of this invention are the thiazide diuretics, e.g., chlorothiazide, hydrochlorothiazide, flumethiazide, hydroflumethiazide, bendroflumethiazide, methylclothiazide, trichloromethiazide, polythiazide or benzthiazide as well as ethacrynic acid, ticrynafen, chlorthalidone, furosemide, musolimine, bumetanide, triamterene, amiloride and spironolactone and salts of such compounds.

The compounds of formula I can be formulated for use in the reduction of blood pressure in compositions such as tablets, capsules or elixirs for oral administration, or in sterile solutions or suspensions for parenteral administration. About 10 to 500 mg of a compound of formula I is compounded with physiologically acceptable vehicle, carrier, excipient, binder, preservatives, stabilizer, flavor, etc., in a unit dosage form as called for by accepted pharmaceutical practice. The amount of active substance in these compositions or preparations is such that a suitable dosage in the range indicated is obtained.

The following examples are illustrative and present preferred embodiments of the invention. Temperatures are given in degrees centigrade. AG-50W-X8 refers to a crosslinked polystyrenedivinylbenzene sulfonic acid cation exchange resin. HP-20 refers to a porous crosslinked polystyrene-divinyl benzene polymer resin.

EXAMPLE 1

($\pm$)-1-[2-[[Hydroxy(4-phenylbutyl)phosphinyl]oxy]-1-oxopropyl]-L-proline, dilithium salt A. (4-Phenylbutyl)phosphonic acid A mixture of 4-phenylbutyl chloride (8.0 g, 47.5 mmole) and triethylphosphite (15.0 ml, 72 mmole) was heated at reflux (bath temperature 185° C.) under argon for 41.5 hours. Distillation of the mixture gave pure diethyl (4-phenylbutyl)phosphonate (10.8 g, 84%) as a colorless liquid, b.p. 152°–154° C. (1.0 mmHg). TLC (EtOAc) single spot $R_f = 0.55$.

A mixture of diethyl (4-phenylbutyl)phosphonate (3.5 g, 13.0 mmole) and 6 N HCl (45 ml) was refluxed under argon for 16 hours. The cooled reaction mixture was extracted with EtOAc. The organic phase was washed with saturated NaCl, dried (MgSO$_4$), and evaporated. The crude product (2.3 g) was recrystallized from diisopropyl ether to give pure (4-phenylbutyl)phosphonic acid (1.7 g, 61%) as white needles, m.p. 92°–93° C.

Analysis Calcd for $C_{10}H_{15}O_3P$: C, 56.07; H, 7.06; P, 14.46. Found: C, 55.83; H, 7.04; P. 14.34.

B.

($\pm$)-2-[[Phenylmethoxy(4-phenylbutyl)phosphinyl]oxy]propionic acid, ethyl ester A mixture of 4-phenylbutyl phosphonic acid from Part A (0.70 g, 3.27 mmole), benzene (10 ml), and PCl$_5$ (1.36 g, 6.54 mmole) was refluxed under argon for 30 minutes. The benzene and POCl$_3$ were removed in vacuo and the residue taken up in CH$_2$Cl$_2$ (5 ml). After cooling to 0° C. (ice-bath), triethylamine (1.3 ml, 9.39 mmole) was added followed by dropwise treatment with d,1 ethyl lactate (0.39 ml, 3.3 mmole) in CH$_2$Cl$_2$ (3 ml) over a 5 minute period. After 1 hour benzyl alcohol (0.35 ml, 3.3 mmole) in CH$_2$Cl$_2$ (3 ml) was added dropwise over 2 minutes, the ice-bath removed, and the reaction mixture allowed to stir for 2 hours. The reaction mixture was diluted with EtOAc then washed with H$_2$O, 5% KHSO$_4$, saturated NaHCO$_3$, brine, dried (MgSO$_4$), and evaporated. The residue (1.3 g) was chromatographed on silica (70 g) eluting with 2/1 hexane/EtOAc to obtain the title compound (0.80 g, 1.98 mmole; 60% yield) as an oil.

TLC (2/1 hexane/EtOAc) two isomers $R_f = 0.25$, 0.20.

C. (±)-2-[[Phenylmethoxy(4-phenylbutyl)phosphinyl]oxy]propionic acid

A mixture of the ethyl ester from Part B (0.80 g, 1.98 mmole), 1 N NaOH (3.0 ml, 3.0 mmole) and dioxane (10 ml) was stirred at 25° C. in an argon atmosphere for 2 hours. The reaction mixture was diluted with $H_2O$ and then washed with EtOAc. The aqueous phase was acidified to pH=1.0 with concentrated HCl and the resulting oil was extracted into EtOAc. The ETOAc extract was washed with brine, dried ($MgSO_4$), and evaporated to give the title compound (0.70 g, 1.86 mmole, 94% yield) as an oil.

TLC (1/9 $CH_3OH/CH_2Cl_2$) major spot $R_f$=0.5.

D. (±)-1-[2-[[Phenylmethoxy(4-phenylbutyl)phosphinyl]oxy]-1-oxopropyl]-L-proline, phenylmethyl ester A mixture of mono acid from Part C (0.70 g, 1.86 mmole), 1,1-carbonyldiimidazole (0.30 g, 1.85 mmole) and dry THF (10 ml) was stirred at 0° C. in an argon atmosphere for 1 hour. Triethylamine (0.26 ml, 1.88 mmole) and L-proline, phenylmethyl ester, hydrochloride salt (commercially available) (0.45 g, 1.86 mmole) were added to the resulting imidazolide and the ice-bath removed. After 60 hours the reaction mixture was diluted with EtOAc, then washed with $H_2O$, 5% $KHSO_4$, saturated $NaHCO_3$, brine, dried ($MgSO_4$), and evaporated. The residue (850 mg) was chromatographed on silica (45 g) eluting with 5/2 hexane/acetone to obtain the title compound (0.40 g, 0.71 mmole, 38% yield) as an oil.

TLC (5/2 hexane/acetone) single spot $R_f$=0.2.

E. (±)-1-[2-[[Hydroxy(4-phenylbutyl)phosphinyl]oxy]-1-oxopropyl]-L-proline, dilithium salt A mixture of the dibenzyl ester from Part D (0.40 g, 0.71 mmole), 10% Pd/C (50 mg), and $CH_3OH$ (40 ml) was hydrogenated on the Parr apparatus at 50 psi for 3 hours. The catalyst was removed by filtration (celite bed) and the filtrate was evaporated. The residue was taken up in $H_2O$ (2 ml) and 0.1 M $Li_2CO_3$ (3.5 ml, 0.35 mmole) and passed through an AG50WX8 (Li) (40 ml) column. The desired fractions were combined, filtered (millipore), and lyophilized to give the title product (245 mg, 0.62 mmole, 87% yield) as a glassy solid.

TLC (7/2/1 isopropanol/conc. $NH_4OH/H_2O$) single spot $R_f$=0.8.

Analysis calcd for $C_{18}H_{24}NO_6P \cdot 2$ Li·1.0 mole $H_2O$: C, 52.31; H, 6.34; N, 3.39; P, 7.5. Found: C, 52.44; H, 6.14; N, 3.63; P, 7.2.

EXAMPLE 2

1-[(S)-2-[[[(±)-1-(Benzoylamino)-3-phenylpropyl]phosphinyl]oxy]-1-oxopropyl]-L-proline, dilithium salt

A. (1-Amino-3-phenylpropyl)phosphonic acid

To a stirred solution of benzyl carbamate (15 g, 0.1 mole) and phosphorus trichloride (9 ml, 0.1 mole) in glacial acetic acid (25 ml) at 0° (ice bath), there is added 3-phenylpropanol (20 g, 0.149 mole) dropwise over a period of 30 minutes. The resulting mixture is stirred at 0° for 15 minutes and then allowed to warm to room temperature. The mixture is then refluxed for 30 minutes, treated with 4 N hydrochloric acid (125 ml) and again refluxed for one hour. After cooling, the aqueous solution is decanted from the dark organic layer, washed with ethyl acetate, and evaporated to dryness. The residue is taken up in water (50 ml) and again evaporated to dryness. This is repeated two more times. Finally, the solid residue is triturated with acetonitrile-water and dried in vacuo over phosphorus pentoxide to give 10.05 g of (1-amino-3-phenylpropyl)phosphonic acid as a white crystalline solid; m.p. 274°-278° (dec.).

B. [3-Phenyl-1-[(benzoylamino)propyl]phosphonic acid

A mixture of amino phosphonic acid prepared in Part A (3.2 g, 14.9 mmole), dioxane (20 ml), $H_2O$ (8.0 ml), and triethylamine (7.5 ml, 54.2 mmole) at 0° C. (ice bath) was treated dropwise with benzoyl chloride (2.8 ml, 19.4 mmole) in dioxane (4.0 ml) over a 5 minute period. The ice bath was removed and the reaction mixture stirred for 2 hours, diluted with $H_2O$, and then washed with $Et_2O$. The aqueous phase was acidified to pH 1.0 with concentrated HCl and the resulting oil was extracted into EtOAc (3x), washed with brine, dried ($MgSO_4$), and evaporated. The residue was stirred under $Et_2O$/hexane to give a gummy solid, from which upon trituration with IPE (2x) the title compound (4.0 g, 12.5 mmole, 84% yield) was obtained as a white crystalline solid, m.p. 166°-168° C.

TLC (7:2:1, Isopropanol/conc. $NH_4OH/H_2O$) major spot, $R_f$=0.4.

Analysis Calcd for $C_{10}H_{13}NO_4P$: N, 4.39; C. 60.10; H, 5.68; P, 9.7. Found: N, 4.34; C, 60.30; H, 5.83; P, 9.6.

C. 1-[(S)-2-Hydroxy-1-oxopropyl]-L-proline, phenylmethyl ester

A mixture of sodium lactate (1.7 g, 15.0 mmole), diphenyl phosphorylazide (3.6 ml, 16.5 mmole) and dry DMF (30 ml) at 0° C. (ice bath) in an argon atmosphere was treated with triethyl amine (2.1 ml, 15.2 mmole) and L-proline, phenylmethyl ester, hydrochloride salt (3.6 g, 15.0 mmole). After 24 hours, the reaction mixture was partitioned between EtOAc and $H_2O$. The aqueous phase was back extracted, the organic extracts combined, washed with 5% $KHSO_4$, brine, and evaporated. The residue (5.0 g) was chromatographed on silica (130 g) eluting the EtOAc/Hexane (1:1) to give the title compound (2.5 g, 9.0 mmole, 60% yield) as a white crystalline solid after evaporation, m.p. 86°-88° C.

Analysis Calcd for $C_{15}H_{19}NO_4$: N, 5.05; C, 64.97; H, 6.91. Found: N, 5.02; C, 64.70; H, 6.85.

D. 1-[(S)-2-[[[(±)-1-(Benzoylamino)-3-phenylpropyl]hydroxyphosphinyl]oxy]-1-oxopropyl-L-proline, phenylmethyl ester A mixture of the phosphonic acid from Part B (0.60 g, 1.9 mmole), lactoyl proline, phenylmethyl ester (from Part C) (0.52 g, 1.9 mmole), and dry THF (5 ml) at 0° C. under argon was treated with dicyclohexylcarbodiimide (0.39 g, 1.9 mmole). After 15 minutes, the reaction mixture was diluted with EtOAc and filtered to remove the dicyclohexylurea. The filtrate was washed with 5% $KHSO_4$, brine, dried ($MgSO_4$), and evaporated. The residue (1.2 g) was chromatographed on silica (60 g) eluting with (20:1:1, $CH_2Cl_2/CH_3OH/HOAc$). The desired fractions were combined and evaporated to dryness to give the title compound (1.0 g, 1.7 mmole, 90% yield) as a foam. TLC: (20:1:1, $CH_2Cl_2/CH_3OH/HOAc$) two isomers $R_f$=0.15, 0.20.

E.

1-[(S)-2-[[[(±)-1-(Benzoylamino)-3-phenylpropyl]phosphinyl]oxy]-1-oxopropyl]-L-proline, dilithium salt A mixture of the phosphonic monoester from Part D (1.0 g, 1.7 mmole), 10% Pd/C (400 mg), and $CH_3OH$ (50 ml) was hydrogenated on the Parr apparatus at 50 psi for 1.5 hours. The catalyst was removed by filtration (Celite bed) and the solvent evaporated. The residue was taken up in 1 N LiOH (2.5 ml, 2.5 mmole) and applied to an AG50Wx8 (Li) (50 ml) column eluting with $H_2O$. The desired fractions were combined, evaporated to small volume, and chromatographed on an HP-20 (200 ml) column eluting with a linear gradient $H_2O/CH_3CN$ (0→90% $CH_3CN$). The desired fractions were combined, evaporated to dryness, taken up in $H_2O$, filtered (millipore), and lyophilized to give the title product (0.51 g, 1.0 mmole, 60% yield) as a white solid. TLC: (7:2:1, Isopropanol/conc. $NH_2OH/H_2O$) single spot $R_f=0.7$, m.p. 248°–255° C.

Analysis Calcd for $C_{24}H_{27}N_2O_7PLi_2 \cdot 0.74$ moles of $H_2O$

Calcd: N, 5.45; C, 56.12; H, 5.59; P, 6.0. Found: N, 5.35; C, 56.12; H, 5.66; P, 6.0.

EXAMPLES 3–105

Following the procedure of Example 1 but employing the phosphonic acid shown in Col. I, the lactate shown in Column II, the imino acid or amino acid or ester in Col. III, and the alcohol $R_3OH$, one obtains the diester shown in Col. IV. Both the $R_3$ and $R_6$ ester groups may be removed to yield the corresponding diacid or salt as set forth in Example 1E or only the carboxylic ester group $R_6$ may be removed or in the case of Examples 77–87 only the $R_3$ ester group may be removed.

| Col. I | Col. III |
|---|---|
| $R_1-\overset{\overset{O}{\|}}{\underset{\underset{OH}{\|}}{P}}-OH$ | $HO-\overset{\overset{R_2}{\|}}{CH}-CO_2alkyl$ |

| Col. III | Col. IV |
|---|---|
| HX | $R_1-\overset{\overset{O}{\|}}{\underset{\underset{OR_3}{\|}}{P}}-O-\overset{\overset{R_2}{\|}}{CH}-\overset{\overset{O}{\|}}{C}-X$ |

| Ex. | $R_1$ | $R_3$ | $R_2$ | X |
|---|---|---|---|---|
| 3. | $H_3C-(CH_2)_5-$ | $-CH_2-\langle Ph \rangle$ | $-(CH_2)_4NH\overset{\overset{O}{\|}}{C}OCH_2-\langle Ph \rangle$ | pyrrolidine-$COOCH_2-\langle Ph \rangle$ (L) |
| 4. | $H_3C-$ | $-CH_2-\langle Ph \rangle$ | $-CH_3$ | pyrrolidine-$COOCH_2-\langle Ph \rangle$ (L) |
| 5. | $H_5C_2-$ | $-CH(\langle Ph \rangle)_2$ | $-H$ | pyrrolidine-$COOCH_2-\langle Ph \rangle$ (L) |
| 6. | phthalimido-$(CH_2)_6-$ | $-CH_2-\langle Ph \rangle$ | $-CH_3$ | pyrrolidine-$COOCH_2-\langle Ph \rangle$ (L) |
| 7. | $\langle Ph \rangle -(CH_2)_4-$, $CH_2Ph$ | $-CH_2-\langle Ph \rangle$ | $-(CH_2)_3-NHC(=NH)NH-NO_2$ | pyrrolidine-$COOCH_2-\langle Ph \rangle$ (L) |
| 8. | $O=\langle Ph \rangle-(CH_2)_3-$ | $-CH_2-\langle Ph \rangle$ | $-CH_3$ | piperidine-$COOCH_2-\langle Ph \rangle$ (L) |

-continued

| Ex. | R₁ | R₃ | R₂ | X |
|---|---|---|---|---|
| 9. | H₃C—C₆H₄— | —CH₂—C₆H₅ | —(CH₂)₂—C₆H₅ | —NH—CH(COOCH₂C₆H₅)— (pyrrolidine, L) |
| 10. | H₃CO—C₆H₄—CH₂— | —CH₂—C₆H₅ | —(CH₂)₄NHC(O)CH₂—C₆H₅ | —NH—CH(COOCH₂C₆H₅)— (pyrrolidine, L) |
| 11. | F—C₆H₄—(CH₂)₂— | —CH₂—C₆H₅ | —CF₃ | —NH—CH(COOCH₂C₆H₅)— (pyrrolidine, L) |
| 12. | 2-Cl-C₆H₄—(CH₂)₄— | —CH₂—C₆H₅ | —CH₃ | —NH—CH(COOCH₂C₆H₅)— (pyrrolidine, L) |
| 13. | H₃CS—C₆H₄—CH₂— | —CH(C₆H₅)₂ | —H | —NH—CH(COOC(CH₃)₃)— (pyrrolidine, L) |
| 14. | C₆H₁₁—(CH₂)₄— | —CH₂—C₆H₅ | —CH₃ | —NH—CH(COOCH₂C₆H₅)— (pyrrolidine, L) |
| 15. | cyclopentyl-CH₂— | —CH₂—C₆H₅ | —CH₃ | —NH—CH(COOCH₂C₆H₅)— (pyrrolidine, L) |
| 16. | 2-thienyl-CH₂— | —CH(C₆H₅)₂ | —CH₃ | —NH—CH(COOC(CH₃)₃)— (pyrrolidine, L) |
| 17. | 3-thienyl— | —CH(C₆H₅)₂ | —CH₃ | —NH—CH(COOC(CH₃)₃)— (pyrrolidine, L) |
| 18. | 2-furyl-CH₂— | —CH₂—C₆H₅ | —CF₃ | —NH—CH(COOCH₂C₆H₅)— (pyrrolidine, L) |
| 19. | 3-furyl-CH₂— | —CH₂—C₆H₅ | —CH₃ | —NH—CH(COOC(CH₃)₃)— (pyrrolidine, L) |
| 20. | 4-pyridyl-CH₂— | —CH₂—C₆H₅ | —CH₃ | —NH—CH(COOCH₂C₆H₅)— (pyrrolidine, L) |

-continued

| Ex. | R₁ | R₃ | R₂ | X |
|---|---|---|---|---|
| 21. | 3-pyridyl-CH₂— | —CH₂—C₆H₅ | —CH₃ | 4-substituted proline benzyl ester (L) |
| 22. | H₃C—(CH₂)₆— | —CH₂—C₆H₅ | —CH₃ | 4-OH proline benzyl ester (L) |
| 23. | H₃C—(CH₂)₃— | —CH₂—C₆H₅ | —CH₃ | 4-OCH₃ proline benzyl ester (L) |
| 24. | C₆H₅— | —CH(C₆H₅)₂ | —CH₃ | 4-SCH₃ proline t-butyl ester (L) |
| 25. | C₆H₅—CH₂— | —CH₂—C₆H₅ | —H | 4-Cl proline benzyl ester (L) |
| 26. | C₆H₅—(CH₂)₂— | —CH₂—C₆H₅ | —CH₃ | 4-F proline benzyl ester (L) |
| 27. | C₆H₅—(CH₂)₄— | —CH₂—C₆H₅ | —CH₃ | 4-CH₃ proline benzyl ester (L) |
| 28. | C₆H₅—(CH₂)₆— | —CH₂—C₆H₅ | —CH₃ | 4-oxo proline benzyl ester (L) |
| 29. | 3,5-(H₃CO)₂C₆H₃—(CH₂)₄— | —CH₂—C₆H₅ | —CH₃ | 4-N₃ proline benzyl ester (L) |
| 30. | 4-Cl-C₆H₄—(CH₂)₃— | —CH₂—C₆H₅ | —CH₃ | 4-N(CH₃)₂ proline benzyl ester (L) |

-continued
| Ex. | R₁ | R₃ | R₂ | X |
|---|---|---|---|---|
| 31. | 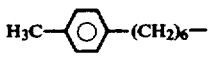 | —CH₂—⌬ | —CH₃ | 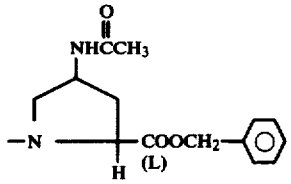 |
| 32. | 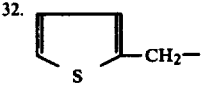 | —CH(⌬)₂ | —CH₃ | 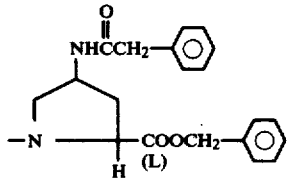 |
| 33. | 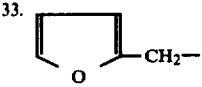 | —CH₂—⌬ | —CH₃ | 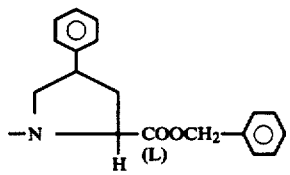 |
| 34. | 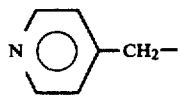 | —CH(⌬)₂ | —CH₃ | 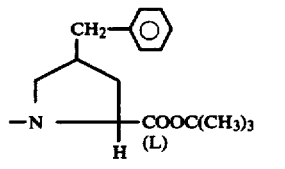 |
| 35. |  | —CH₂—⌬ | —CH₃ | 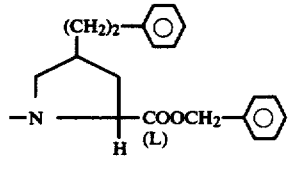 |
| 36. | H₃C— | —CH₂—⌬ | —CH₃ | 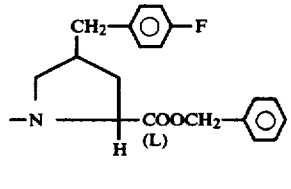 |
| 37. | H₅C₂— | —CH(⌬)₂ | —CH₃ | 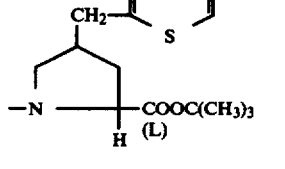 |
| 38. | 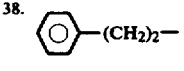 | —CH₂—⌬ | —CH₃ | 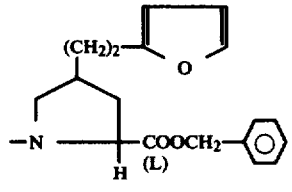 |

-continued

| Ex. | R₁ | R₃ | R₂ | X |
|---|---|---|---|---|
| 39. | thiophen-2-yl-CH₂— | —CH(C₆H₅)₂ | —CH₃ | cyclohexyl-substituted —N—CH(COOC(CH₃)₃)— (L) |
| 40. | furan-2-yl-CH₂— | —CH₂C₆H₅ | —CH₃ | naphth-2-yl-CH₂— substituted —N—CH(COOCH₂C₆H₅)— (L) |
| 41. | pyridin-4-yl-CH₂— | —CH₂C₆H₅ | —CH₃ | biphenyl-CH₂— substituted —N—CH(COOCH₂C₆H₅)— (L) |
| 42. | H₃C—(CH₂)₅— | —CH₂C₆H₅ | —H | —O—C(=O)NH₂ substituted —N—CH(COOCH₂C₆H₅)— (L) |
| 43. | C₆H₅—(CH₂)₄— | —CH₂C₆H₅ | —CH₃ | 4-F-C₆H₄—O— substituted —N—CH(COOCH₂C₆H₅)— (L) |
| 44. | C₆H₅— | —CH₂C₆H₅ | —(CH₂)₄NHC(=O)CH₂C₆H₅ | C₆H₅—CH₂—O— substituted —N—CH(COOCH₂C₆H₅)— (L) |
| 45. | C₆H₅—CH₂— | —CH(C₆H₅)₂ | —CH₃ | C₆H₅—CH₂—S— substituted —N—CH(COOC(CH₃)₃)— (L) |
| 46. | C₆H₅—(CH₂)₂— | —CH(C₆H₅)₂ | —CH₃ | C₆H₅—S— substituted —N—CH(COOC(CH₃)₃)— (L) |

-continued

| Ex. | $R_1$ | $R_3$ | $R_2$ | X |
|---|---|---|---|---|
| 47. | Ph-(CH$_2$)$_4$- | -CH$_2$-Ph | -CH$_3$ | -N(H)-CH(COOCH$_2$Ph)-CH$_2$-CH(S-C$_6$H$_4$-F)- (L) |
| 48. | Ph-(CH$_2$)$_4$- | -CH(Ph)$_2$ | -CH$_3$ | -N(H)-CH(COOC(CH$_3$)$_3$)-CH$_2$-CH(S-naphthyl)- (L) |
| 49. | H$_3$C-(CH$_2$)$_3$- | -CH(Ph)$_2$ | -CH$_3$ | -N(H)-CH(COOC(CH$_3$)$_3$)-CH$_2$-CH(S-C$_6$H$_4$-Ph)- (L) |
| 50. | H$_3$CO-C$_6$H$_4$-(CH$_2$)$_4$- | -CH$_2$-Ph | -CH$_3$ | -N(H)-CH(COOCH$_2$Ph)-CH$_2$-CH(O-naphthyl)- (L) |
| 51. | Ph-(CH$_2$)$_2$- | -CH$_2$-Ph | -CH$_3$ | -N(H)-CH(COOCH$_2$Ph)-CH$_2$-CH(Cl)- (L) |
| 52. | Ph- | -CH$_2$-Ph | -CH$_3$ | -N(H)-CH(COOCH$_2$Ph)-CH$_2$-CH(OC(O)N(CH$_3$)$_2$)- (L) |
| 53. | Ph-(CH$_2$)$_4$- | -CH$_2$-Ph | -CH$_3$ | -N(H)-CH(COOCH$_2$Ph)-CH$_2$-CH(O-Ph)- (L) |
| 54. | Ph-(CH$_2$)$_3$- | -CH(Ph)$_2$ | -CH$_3$ | -N(H)-CH(COOCH(Ph)$_2$)-CH$_2$-CH(S-Ph)- (L) |
| 55. | Ph-(CH$_2$)$_5$- | -CH(Ph)$_2$ | -CH$_3$ | -N(H)-CH(COOCH(Ph)$_2$)-CH$_2$-CH(S-CH$_2$-Ph)- (L) |
| 56. | H$_3$C-(CH$_2$)$_3$- | -CH$_2$-Ph | -CH$_3$ | pyroglutamyl -COOCH$_2$Ph (L) |

-continued
| Ex. | R₁ | R₃ | R₂ | X |
|---|---|---|---|---|
| 57. | —(CH₂)₄— | —CH₂— | —CH₃ |  |
| 58. | —(CH₂)₂— | —CH₂— | —CH₃ | 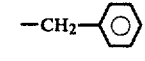 |
| 59. | H₃C—(CH₂)₅— | —CH₂— | —CH₃ | 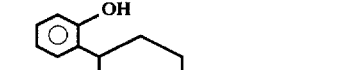 |
| 60. | 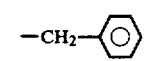—CH₂— | —CH(—)₂ | —CH₃ | 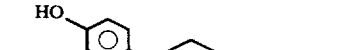 |
| 61. | —CH₂— | —CH₂—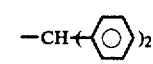 | —CH₃ |  |
| 62. | —(CH₂)₄— | —CH(—)₂ | —H | 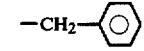 |
| 63. | —(CH₂)₂— | —CH₂—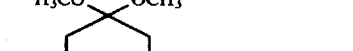 | —CH₃ |  |
| 64. | 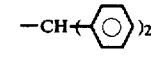 | —CH₂(—)₂ | —CH₃ |  |
| 65. | H₃C—(CH₂)₄— | —CH₂— | —CH₃ | 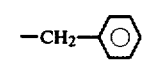 |

-continued

| Ex. | R₁ | R₃ | R₂ | X |
|---|---|---|---|---|
| 66. | H₃CS—⬡—CH₂— | —CH(⬡)₂ | —H | ![structure with gem-dimethyl dithiane, —N(H)—COOCH(⬡)₂ (L)] |
| 67. | ⬡—(CH₂)₂— | —CH₂—⬡ | —CH₃ | ![tetrahydropyridine with —N—C(H)—COOCH₂⬡ (L)] |
| 68. | ⬡—(CH₂)₄— | —CH(⬡)₂ | —C₂H₅ | ![thiazolidine with —N—C(H)—COOC(CH₃)₃ (L)] |
| 69. | ⬡—(CH₂)₂— | —CH(⬡)₂ | —CH₃ | ![thiazolidine gem-dimethyl with —N—C(H)—COOC(CH₃)₃ (L)] |
| 70. | H₃C—(CH₂)₅— | —CH(⬡)₂ | —CH₃ | ![phenyl-thiazolidine with —N—C(H)—COOC(CH₃)₃ (L)] |
| 71. | ⬡—(CH₂)₄— | —CH₂—⬡ | —CH₃ | ![piperidine-2-carboxylate —N—COOCH₂⬡] |
| 72. | ⬡—(CH₂)₂— | —CH₂—⬡ | —CH₃ | ![tetrahydroisoquinoline —N—C(H)—COOCH₂⬡] |
| 73. | ⬡— | —CH₂—⬡ | —CH₃ | ![tetrahydroisoquinoline —N—C(H)—COOCH₂⬡] |
| 74. | ⬡—(CH₂)₂— | —CH₂—⬡ | —CH₃ | ![tetrahydroquinoline —N—C(H)—COOCH₂⬡] |

4,452,790
-continued
| Ex. | R₁ | R₃ | R₂ | X |
|---|---|---|---|---|
| 75. | —(CH₂)₄— | —CH₂— | —CH₃ | 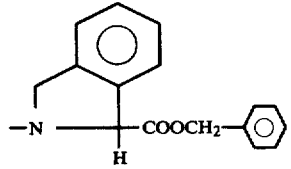 |
| 76. | H₃C—(CH₂)₅— | —CH₂—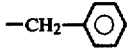 | —H | 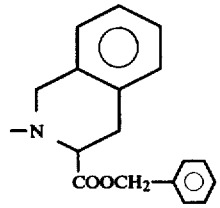 |
| 77. | —(CH₂)₄— | —CH₂— | —CH₃ | 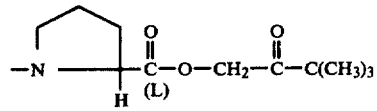 |
| 78. | —(CH₂)₂— | —CH()₂ | —CH₃ | 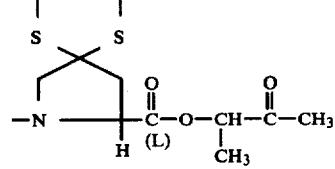 |
| 79. | H₃C—(CH₂)₅— | —CH₂— | —CH₃ | 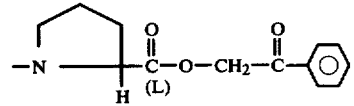 |
| 80. | —(CH₂)₂— | —CH()₂ | —CH₃ | 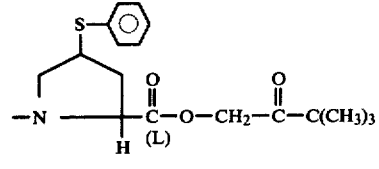 |
| 81. | 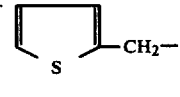—CH₂— | —CH()₂ | —CH₃ | 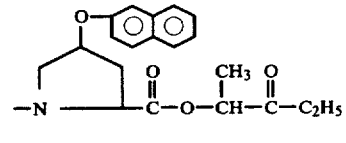 |
| 82. | —(CH₂)₄— | —CH₂— | —CH₃ | 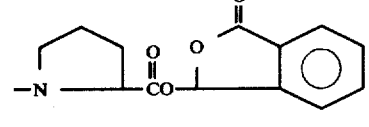 |
| 83. | —(CH₂)₄— | —CH₂— | —CH₃ | 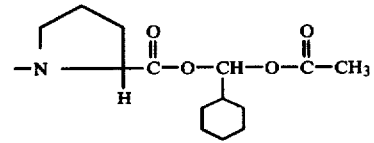 |

-continued

| Ex. | R₁ | R₃ | R₂ | X |
|---|---|---|---|---|
| 84. | Ph-(CH₂)₂- | -CH₂-Ph | -CH₃ | -N-CH(cyclohexyl)-C(=O)-O-CH-O-C(=O)-C₂H₅ (ring from N) |
| 85. | Ph-(CH₂)₄- | -CH₂-Ph | -CH₃ | -N(Ph)-CH₂-COOCH₂-Ph |
| 86. | Ph-(CH₂)₂- | -CH₂-Ph | -CH₃ | -NH-CH(CH₂CH(CH₃)₂)-COOCH₂-Ph (L) |
| 87. | Ph- | -CH₂-Ph | -CH₃ | -N(CH₃)-CH₂-COOCH₂-Ph |
| 88. | Ph-(CH₂)₂- | -CH₂-Ph | -CH₃ | -N(cyclopentyl)-CH₂-COOCH₂-Ph |
| 89. | Ph-(CH₂)₄- | -CH₂-Ph | -CH₃ | -N((CH₂)₂Ph)-CH₂-COOCH₂-Ph |
| 90. | H₃C-(CH₂)₅- | -CH(Ph)₂ | -H | -NH-CH(CH₃)-COOCH₂-Ph (L) |
| 91. | Ph-(CH₂)₄- | -CH₂-Ph | -CH₃ | -NH-CH(CH₂Ph)-COOCH₂-Ph (L) |
| 92. | Ph-(CH₂)₂- | -CH₂-Ph | -CH₃ | -NH-CH(CH₂-C₆H₄-OCH₂Ph)-COOCH₂-Ph (L) |
| 93. | Ph- | -CH(Ph)₂ | -CH₃ | -N(Ph)-CH₂-COOCH₂-Ph |

-continued

| Ex. | R₁ | R₃ | R₂ | X |
|---|---|---|---|---|
| 94. | H₅C₂— | —CH₂—C₆H₅ | —CH₃ | —NH—CH(COOCH₂C₆H₅)—CH₂-(3-indolyl) (L) |
| 95. | C₆H₅— | —CH₂—C₆H₅ | —CH₃ | —NH—CH(COOCH₂C₆H₅)—CH₂-(1-benzylimidazol-4-yl) (L) |
| 96. | cyclopentyl-CH₂— | —CH₂—C₆H₅ | —CH₃ | —NH—CH(COOCH₂C₆H₅)—(CH₂)₄—NHCOCH₂C₆H₅ (L) |
| 97. | (2-thienyl)-CH₂— | —CH(C₆H₅)₂ | —CH₃ | —NH—CH(COOCH₂C₆H₅)—CH₂—SCH₂C₆H₅ (L) |
| 98. | (2-furyl)-CH₂— | —CH₂—C₆H₅ | —CH₃ | —NH—CH(COOCH₂C₆H₅)—(CH₂)₂—S—CH₃ (L) |
| 99. | C₆H₅—(CH₂)₂— | —CH₂—C₆H₅ | —CH₃ | —NH—CH(COOCH₂C₆H₅)—(CH₂)₃—NHC(=NH)NH—NO₂ (L) |
| 100. | C₆H₅—(CH₂)₄— | —CH(C₆H₅)₂ | —CH₃ | —NH—CH(COOCH₂C₆H₅)—CH₂—C(=O)—NH₂ |
| 101. | H₃C—(CH₂)₅— | —CH₂—C₆H₅ | —CH₃ | —N(cyclohexyl)—CH₂—COOCH₂C₆H₅ |
| 102. | C₆H₅—(CH₂)₂— | —CH₂—C₆H₅ | H | —NH—CH(COOCH₂C₆H₅)—CH₃ (L) |
| 103. | H₃C—(CH₂)₅— | —CH₂—C₆H₅ | CH₃ | —NH—CH(COOCH₂C₆H₅)—CH₂—C₆H₄—OCH₂C₆H₅ (L) |
| 104. | H₃C—CH₂— | —CH₂—C₆H₅ | C₂H₅ | —NH—CH₂—COOCH₂C₆H₅ |

-continued

| Ex. | R₁ | R₃ | R₂ | X |
|---|---|---|---|---|
| 105. | Ph–(CH₂)₄– | –CH₂–Ph | H | –NH–CH(CH₂Ph)–COOCH₂–Ph (L) |

EXAMPLES 106 TO 124

Following the procedure of Example 2 but employing the phosphonic acid shown in Col. I, the acid chloride shown in Col. II, and the hydroxyacyl imino ester shown in Col. III, one obtains the intermediate shown in Col. IV. Removal of the carboxylic acid protecting group yields the compound of Col. V which can be treated to obtain a salt as shown in Example 2, Part E.

Col. I:  $H_2N-CH(R_{19})-P(=O)(OH)-OH$

Col. II:  $R_{20}-C(=O)-Cl$

Col. III:  $HO-CH(R_2)-C(=O)-X$

Col. IV:  $R_{20}-C(=O)-NH-CH(R_{19})-P(=O)(OH)-O-CH(R_2)-C(=O)-X$

Col. V:  $R_{20}-C(=O)-NH-CH(R_{19})-P(=O)(OH)-O-CH(R_2)-C(=O)-X$

| Ex. | R₁₉ | R₂ | X | R₂₀ |
|---|---|---|---|---|
| 106. | –(CH₂)₂–Ph | –CH₃ | pyrrolidine-N–CH(COOCH₂Ph)– (L) | Ph–CH₂– |
| 107. | –(CH₂)₂–Ph | –CH₃ | pyrrolidine-N–CH(COOCH₂Ph)– (L) | Ph–(CH₂)₂– |
| 108. | –(CH₂)₂–Ph | –CH₃ | pyrrolidine-N–CH(COOCH₂Ph)– (L) | H₃C– |
| 109. | –CH₂–Ph | –CH₃ | pyrrolidine-N–CH(COOCH₂Ph)– (L) | tetrahydrofuranyl (O) |
| 110. | –(CH₂)₂–Ph | –CH₃ | pyrrolidine-N–CH(COOCH₂Ph)– (L) | H₃C–C₆H₄– |
| 111. | –Ph | –CH₃ | pyrrolidine-N–CH(COOCH₂Ph)– (L) | F₃C– |

-continued

| Ex. | R₁₉ | R₂ | X | R₂₀ |
|---|---|---|---|---|
| 112. | —(CH₂)₂—C₆H₅ | —CH₃ | pyrrolidine-COOCH₂-phenyl (L, H) | H— |
| 113. | —CH₃ | —CH₃ | pyrrolidine-COOCH₂-phenyl (L, H) | phenyl |
| 114. | —(CH₂)₂—C₆H₅ | —CH₃ | pyrrolidine-COOCH₂-phenyl (L, H) | phenyl |
| 115. | —CH₂-(thiophen-2-yl) | —CH₃ | pyrrolidine-COOCH₂-phenyl (L, H) | Cl-phenyl |
| 116. | —(CH₂)₂-(furan-2-yl) | —CH₃ | pyrrolidine-COOCH₂-phenyl (L, H) | CH₂-phenyl-O-phenyl-CH₂— |
| 117. | —(CH₂)₂—C₆H₅ | —CH₃ | pyrrolidine-COOCH₂-phenyl (L, H) | pyridin-4-yl-CH₂— |
| 118. | —H | —CH₃ | pyrrolidine-COOCH₂-phenyl (L, H) | thiophen-2-yl |
| 119. | —(CH₂)₂—C₆H₅ | —(CH₂)₄NHCOCH₂—C₆H₅ (with C=O) | pyrrolidine-COOCH₂-phenyl (L, H) | phenyl |
| 120. | —(CH₂)₂—C₆H₅ | —CH₃ | dithiolane-pyrrolidine-COOCH₂-phenyl (L, H) | phenyl |
| 121. | —(CH₂)₂—C₆H₅ | —H | pyrrolidine-COOCH₂-phenyl (L, H) | tetrahydrofuran-2-yl-CH₂— |

-continued

| Ex. | R₁₉ | R₂ | X | R₂₀ |
|---|---|---|---|---|
| 122. | —(CH$_2$)$_2$—C$_6$H$_5$ | —H | —N(H,L)—(CH$_2$)$_3$—CH(COOCH$_2$—C$_6$H$_5$)— | —C$_6$H$_5$ |
| 123. | —(CH$_2$)$_2$—C$_6$H$_5$ | —C$_2$H$_5$ | —N(H,L)—CH$_2$-(o-C$_6$H$_4$)-CH(COOCH$_2$—C$_6$H$_5$)— | —C$_6$H$_5$ |
| 124. | —(CH$_2$)$_2$—C$_6$H$_5$ | —CH$_3$ | —NH—CH$_2$—COOCH$_2$— | —C$_6$H$_5$ |

EXAMPLE 125

(±)-1-[2-[[[(2,2-Dimethyl-1-oxopropoxy)methoxy](4-phenylbutyl)phosphinyl]oxy]-1-oxopropyl]-L-proline

A.

(±)-1-[2-[[Phenylmethoxy(4-phenylbutyl)phosphinyl]oxy]-1-oxopropyl]-L-proline, 1,1-dimethylethyl ester Following the procedure of Example 1, Part D, using L-proline, 1,1-dimethylethyl ester in place of L-proline, phenylmethyl ester gives the title compound.

B.

(±)-1-[2-[[Hydroxy(4-phenylbutyl)phosphinyl]oxy]-1-oxopropyl]-L-proline, 1,1-dimethylethyl ester A mixture of the benzyl ester from Part A (1.03 g, 2.0 mmole) 10% Pd/C (0.20 g) and methanol (50 ml) is hydrogenated on a Parr apparatus at a pressure of 50 psi for 3 hours. The catalyst is removed by filtration through celite and the filtrate evaporated to dryness to give the title compound.

C.

(±)-1-[2-[[[(2,2-Dimethyl-1-oxopropyl)methoxy](4-phenylbutyl)phosphinyl]oxy]-1-oxopropyl]-L-proline, 1,1-dimethylethyl ester A solution of the monoacid from Part B (0.64 g, 1.5 mmole), triethylamine (0.42 ml, 3.0 mmole) and chloromethyl pivalate (0.45 g, 3.0 mmole) in dry dimethylformamide (5 ml) is stirred at room temperature under argon for 16 hours. The mixture is then partitioned between EtOAc-water. The organic phase is washed successively with 5% KHSO$_4$, saturated NaHCO$_3$ and saturated NaCl, dried over Na$_2$SO$_4$ and evaporated. The crude product is purified by flash chromatography on silica gel to give the title compound.

D.

(±)-1-[2-[[[(2,2-Dimethyl-1-oxopropoxy)methoxy](4-phenylbutyl)phosphinyl]oxy]-1-oxopropyl]-L-proline A solution of the diester from Part C (0.54 g, 1.0 mmole) and anisole (2 ml) in CH$_2$Cl$_2$ (10 ml) is treated with trifluoroacetic acid (5 ml) at 0° C. (ice bath). After 1 hour at 0° C., the mixture is partitioned between EtOAc-water. The organic phase is washed with water and saturated NaCl, dried over Na$_2$SO$_4$ and evaporated.

The crude product is purified by flash chromatography on silica gel to give the title compound.

EXAMPLES 126–130

Following the procedure of Example 125 but employing the alkylating agent shown in Col. I in place of the chloromethyl pivalate, one obtains the product in Col. II.

| Ex. | Col. I | Col. II |
|---|---|---|
| 126. | BrCH$_2$OC(=O)—CH$_3$ | (±)-1-[2-[[[(Acetyloxy)methoxy](4-phenylbutyl)phosphinyl]oxy]-1-oxopropyl]-L-proline |
| 127. | Cl—CH(CH$_3$)—O—COC$_2$H$_5$ (=O) | (±)-1-[2-[[[1-(Ethoxycarbonyloxy)ethoxy](4-phenylbutyl)phosphinyl]oxy]-1-oxopropyl]-L-proline |
| 128. | Br-CH(benzofuranone) | (±)-1-[2-[[(3-Oxo-1-isobenzofuranyloxy)(4-phenylbutyl)phosphinyl]oxy]-1-oxopropyl]-L-proline |
| 129. | ClCH$_2$O—C(=O)—C$_6$H$_5$ | (±)-1-[2-[[[(Benzoyloxy)methoxy](4-phenylbutyl)phosphinyl]oxy]-1-oxopropyl]-L-proline |
| 130. | Cl—CH(CH(CH$_3$)$_2$)—O—C(=O)—C$_2$H$_5$ | (±)-1-[2-[[[2-Methyl-1-(1-oxopropoxy)propoxy](4-phenylbutyl)phosphinyl]oxy]-1-oxopropyl]-L-proline |

Similarly, the alkylating agents of Examples 125–130 can be employed with the appropriately protected compounds of Examples 1 to 124 to yield other compounds within the scope of this invention. In the cases where the proline carboxyl group is protected as its phenylmethyl ester rather than its t-butyl ester, it is removed by hydrogenation in the presence of Pd/C in the final step.

EXAMPLE 131

(±)-[2-[[Hydroxy(4-phenylbutyl)phosphinyl]oxy]-1-oxopropyl]-L-proline, disodium salt Following the procedure of Example 1 but substituting AG-50W-X8 (Na+) for the lithium resin in Part E, one obtains the title product.

This procedure can be employed in Examples 2-130 to give the corresponding mono or disodium salt. Similarly, by employing a potassium resin the corresponding mono or dipotassium salt is obtained.

EXAMPLE 132

1000 Tablets each containing the following ingredients:

| | |
|---|---|
| (±)-[2-[[Hydroxy(4-phenylbutyl)-phosphinyl]oxy]-1-oxopropyl]-L-proline, disodium salt | 100 mg |
| Corn starch | 50 mg |
| Gelatin | 7.5 mg |
| Avicel (microcrystalline cellulose) | 25 mg |
| Magnesium stearate | 2.5 mg |
| | 185 mg | are prepared from sufficient bulk quantities by mixing the (±)-[2-[[hydroxy(4-phenylbutyl)phosphinyl]oxy]-1-oxopropyl]-L-proline, disodium salt and corn starch with an aqueous solution of the gelatin. The mixture is dried and ground to a fine powder. The Avicel and then the magnesium stearate are admixed with granulation. This mixture is then compressed in a tablet to form 1000 tablets each containing 100 mg of active ingredient.

In a similar manner, tablets containing 100 mg of the product of any of Examples 2 to 130 can be prepared.

EXAMPLE 133

1000 tablets each containing the following ingredients:

| | |
|---|---|
| 1-[(S)—2-[[[(±)-1-(Benzoylamino)-3-phenylpropyl]phosphinyl]oxy]-1-oxopropyl]-L-proline, sodium salt | 50 mg |
| Lactose | 25 mg |
| Avicel | 38 mg |
| Corn starch | 15 mg |
| Magnesium stearate | 2 mg |
| | 130 mg | are prepared from sufficient bulk quantities by mixing the 1-[(S)-2-[[[(±)-1-(benzoylamino)-3-phenylpropyl]phosphinyl]oxy]-1-oxopropyl]-L-proline, sodium salt, lactose and Avicel and then blending with the corn starch. Magnesium stearate is added and the dry mixture is compressed in a tablet press to form 1000 tablets each containing 50 mg of active ingredient. The tablets are coated with a solution of Methocel E 15 (methyl cellulose) including as a color a lake containing yellow #6.

In a similar manner, tablets containing 50 mg of the product of any of Examples 1 and 3 to 130 can be prepared.

EXAMPLE 134

Two piece #1 gelatin capsules each containing 100 mg of 1-[(S)-2-[[[(±)-1-(benzoylamino)-3-phenylpropyl]phosphinyl]oxy]-1-oxopropyl]-L-proline, sodium salt are filled with a mixture of the following ingredients:

| | |
|---|---|
| 1-[(S)—2-[[[(±)-1-(Benzoylamino)-3-phenylpropyl]phosphinyl]oxy]-1-oxopropyl]-L-proline, sodium salt | 100 mg |
| Magnesium stearate | 7 mg |
| Lactose | 193 mg |
| | 300 mg |

In a similar manner, capsules containing 100 mg of the product of any of Examples 1 and 3 to 130 can be prepared.

EXAMPLE 135

An injectable solution is prepared as follows:

| | |
|---|---|
| (±)-1-[2-[[Hydroxy(4-phenylbutyl)-phosphinyl]oxy]-1-oxopropyl]-L-proline, disodium salt | 500 g |
| Methyl paraben | 5 g |
| Propyl paraben | 1 g |
| Sodium chloride | 25 g |
| Water for injection | 5 l |

The active substance, preservatives, and sodium chloride are dissolved in 3 liters of water for injection and then the volume is brought up to 5 liters. The solution is filtered through a sterile filter and asceptically filled into presterilized vials which are closed with presterilized rubber closures. Each vial contains 5 ml of solution in a concentration of 100 mg of active ingredient per ml of solution for injection.

In a similar manner, an injectable solution containing 100 mg of active ingredient per ml of solution can be prepared for the product of any of Examples 2 to 130.

EXAMPLE 136

1000 Tablets each containing the following ingredients:

| | |
|---|---|
| (±)-1-[2-[[Hydroxy(4-phenylbutyl)-phosphinyl]oxy]-1-oxopropyl]-L-proline, disodium salt | 100 mg |
| Avicel | 100 mg |
| Hydrochlorothiazide | 12.5 mg |
| Lactose | 113 mg |
| Corn starch | 17.5 mg |
| Stearic acid | 7 mg |
| | 350 mg | are prepared from sufficient bulk quantities by slugging the (±)-1-[2-[[hydroxy(4-phenylbutyl)phosphinyl]oxy]-1-oxopropyl]-L-proline, disodium salt, Avicel and a portion of the stearic acid. The slugs are ground and passed through a #2 screen, then mixed with the hydrochlorothiazide, lactose, corn starch, and remainder of the stearic acid. The mixture is compressed into 350 mg capsule shaped tablets in a tablet press. The tablets are scored for dividing in half.

In a similar manner, tablets can be prepared containing 100 mg of the product of any of Examples 2 to 130.

What is claimed is:

1. A compound of the formula

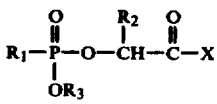

and pharmaceutically acceptable salts thereof wherein:

X is 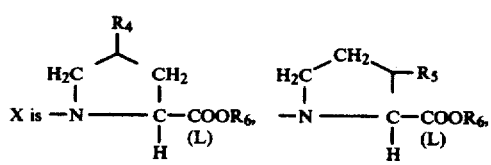

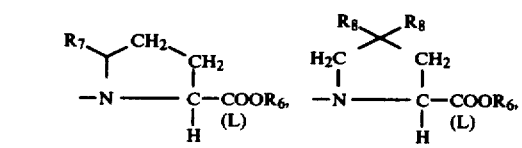

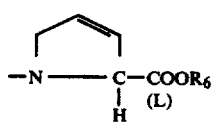

$R_4$ is hydrogen, lower alkyl, halogen, keto, hydroxy,

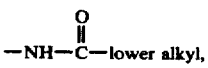

azido, amino,

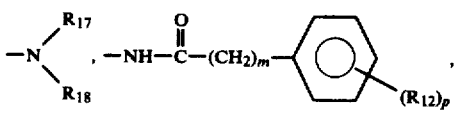

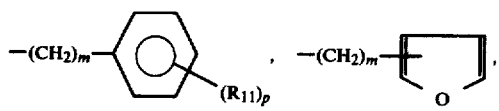

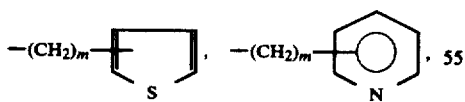

a 1- or 2-naphthyl of the formula

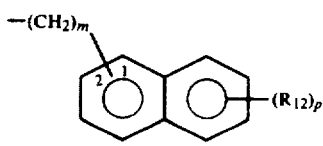

—(CH$_2$)$_m$—cycloalkyl,

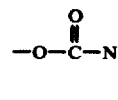

—O—lower alkyl,

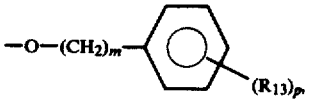

a 1- or 2-naphthyloxy of the formula

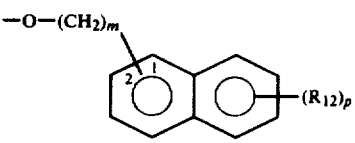

—S—lower alkyl,

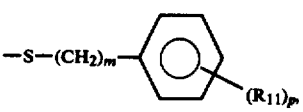

or a 1- or 2-naphthylthio of the formula

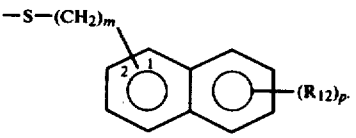

$R_5$ is keto, halogen,

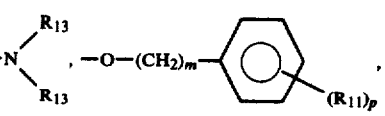

—O—lower alkyl, a 1- or 2-naphthyloxy of the formula

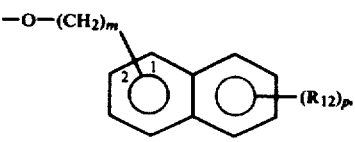

—S—lower alkyl,

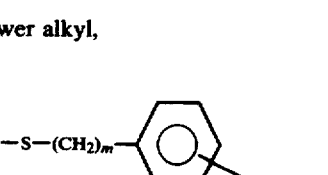

or a 1- or 2-naphthylthio of the formula

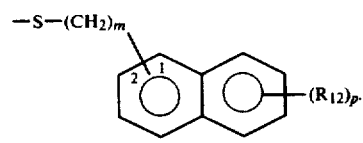

$R_7$ is keto or

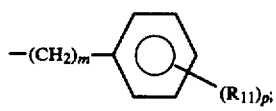

each $R_8$ is the same or different and is halogen or $-Y-R_{14}$;

$R_{11}$ is hydrogen, lower alkyl of 1 to 4 carbons, lower alkoxy of 1 to 4 carbons, lower alkylthio of 1 to 4 carbons, chloro, bromo, fluoro, trifluoromethyl, hydroxy, phenyl, phenoxy, phenylthio, or phenylmethyl;

$R_{12}$ is hydrogen, lower alkyl of 1 to 4 carbons, lower alkoxy of 1 to 4 carbons, lower alkylthio of 1 to 4 carbons, chloro, bromo, fluoro, trifluoromethyl, or hydroxy;

m is zero, one, two or three;

p is one, two or three provided that p is more than one only if $R_{11}$ or $R_{12}$ is hydrogen, methyl, methoxy, chloro, or fluoro;

$R_{13}$ is hydrogen or lower alkyl of 1 to 4 carbons;

Y is oxygen or sulfur;

$R_{14}$ is lower alkyl of 1 to 4 carbons,

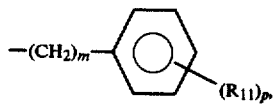

or the $R_{14}$ groups join to complete an unsubstituted 5- or 6-membered ring or said ring in which one or more of the carbons has a lower alkyl of 1 to 4 carbons or a di(lower alkyl of 1 to 4 carbons) substituent;

$R_1$ is alkyl of 1 to 10 carbons, aminoalkyl, haloalkyl,

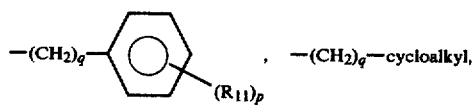

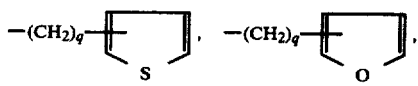

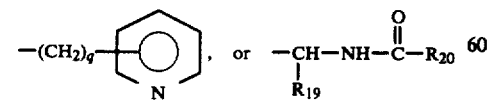

wherein q is zero or an integer from 1 to 7 and $R_{11}$ and p are as defined above; and $R_{19}$ and $R_{20}$ are independently selected from the group consisting of hydrogen, lower alkyl, halo substituted lower alkyl,

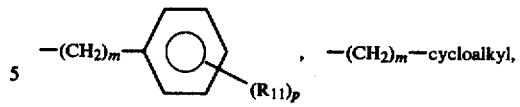

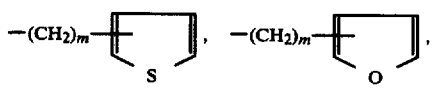

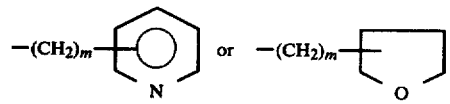

wherein m, $R_{11}$ and p are as defined above;

$R_2$ is hydrogen, lower alkyl, halo substituted lower alkyl,

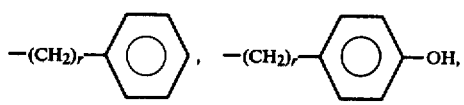

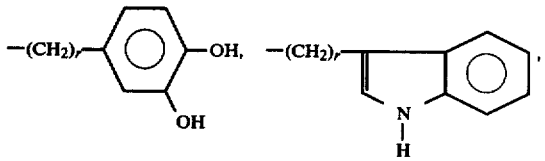

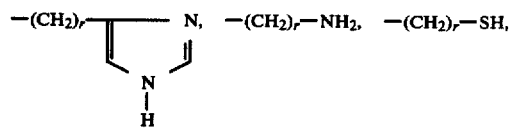

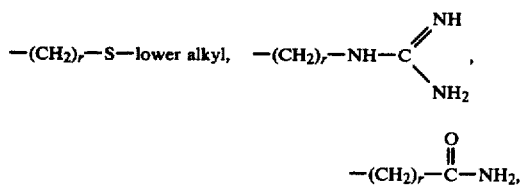

wherein r is as defined hereinbefore;

$R_3$ and $R_6$ are independently selected from hydrogen, lower alkyl, benzyl, benzhydryl, alkali metal, or

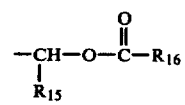

wherein $R_{15}$ is hydrogen, lower alkyl, cycloalkyl, or phenyl, and $R_{16}$ is hydrogen, lower alkyl, lower alkoxy, phenyl, or $R_{15}$ and $R_{16}$ taken together are $-(CH_2)_2-$, $-(CH_2)_3$, $-CH=CH-$ or

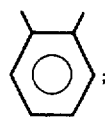

$R_{17}$ is lower alkyl, benzyl, or phenethyl; and $R_{18}$ is hydrogen, lower alkyl, benzyl, or phenethyl.

2. A compound of claim 1 wherein:

$R_4$ is hydrogen, hydroxy, chloro, fluoro, lower alkyl of 1 to 4 carbons, cyclohexyl, amino, —O—lower alkyl wherein lower alkyl is of 1 to 4 carbons,

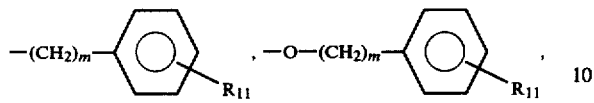

1- or 2-naphthyloxy, —S—lower alkyl wherein lower alkyl is of 1 to 4 carbons,

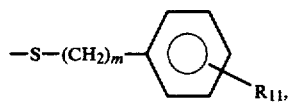

or 1- or 2-naphthylthio;

$R_5$ is —O—lower alkyl wherein lower alkyl is of 1 to 4 carbons, —S—lower alkyl wherein lower alkyl is of 1 to 4 carbons,

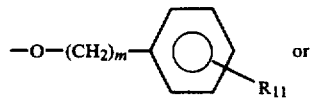 or

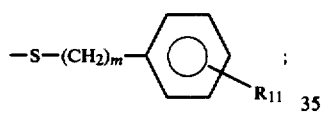

$R_7$ is phenyl, 2-hydroxyphenyl, or 4-hydroxyphenyl;
each $R_8$ is fluoro, chloro or —Y—$R_{14}$;
Y is oxygen or sulfur;
$R_{14}$ is lower alkyl of 1 to 4 carbons or the $R_{14}$ groups join to complete an unsubstituted 5- or 6-membered ring or said ring in which one or more of the carbons has a methyl or dimethyl substituent;
m is zero, one or two;
$R_{11}$ is hydrogen, methyl, methoxy, methylthio, chloro, bromo, fluoro, or hydroxy;
$R_2$ is hydrogen, lower alkyl of 1 to 4 carbons, $CF_3$, or amino substituted lower alkyl of 1 to 4 carbons;
$R_1$ is alkyl of 1 to 10 carbons,

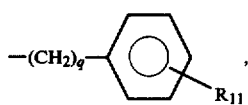

—$(CH_2)_q$—cycloalkyl wherein cycloalkyl is of 5 or 6 carbons,

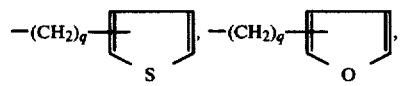

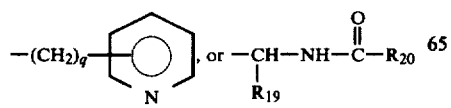

wherein q is zero or an integer from 1 to 4 and $R_{11}$ is as defined above;

$R_{19}$ and $R_{20}$ are independently selected from lower alkyl of 1 to 4 carbons or

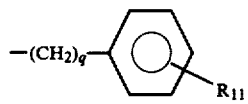

wherein q and $R_{11}$ are as defined above;

$R_3$ and $R_6$ are independently selected from hydrogen, alkali metal salt, lower alkyl of 1 to 4 carbons, or

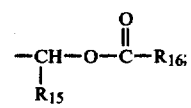

$R_{15}$ is hydrogen, methyl or isopropyl; and
$R_{16}$ is lower alkyl of 1 to 4 carbons or phenyl.

3. A compound of claim 2 wherein X is

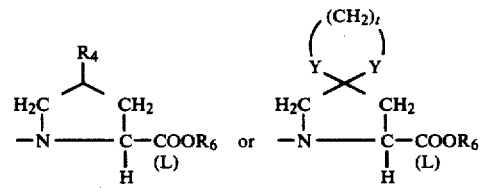

$R_4$ is hydrogen, cyclohexyl, lower alkoxy of 1 to 4 carbons,

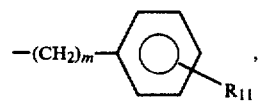

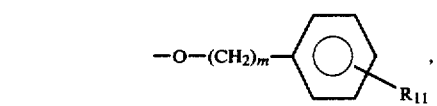

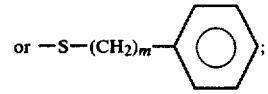

m is zero, one or two;
$R_{11}$ is hydrogen, methyl, methoxy, methylthio, bromo, fluoro, or hydroxy;
Y is oxygen or sulfur;
t is two or three; and
$R_6$ is hydrogen,

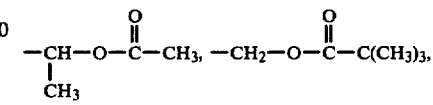

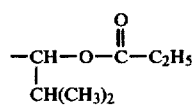

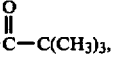

or an alkali metal salt,
R₁ is

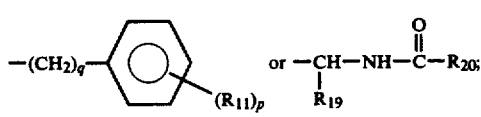

R₂ is hydrogen or lower alkyl; and R₃ is hydrogen, alkali metal or phenylalkyl.

4. A compound of claim 3 wherein R₁ is phenylalkyl or

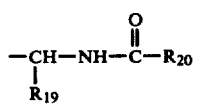

wherein R₁₉ is phenylalkyl and R₂₀ is phenyl; R₂ is hydrogen, methyl, or —(CH₂)₄—NH₂; and R₃ is hydrogen, phenylmethyl,

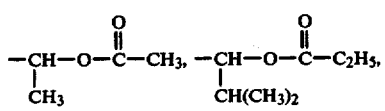

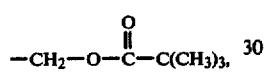

or an alkali metal salt.

5. A compound of claim 4 wherein R₁ is alkyl of 1 to 10 carbons.

6. A compound of claim 5 wherein X is

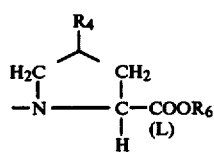

and R₄ is hydrogen.

7. The compound of claim 3 wherein R₁ is phenylbutyl; R₂ is methyl; and R₃ and R₆ are an alkali metal salt.

8. The compound of claim 3 wherein R₁ is

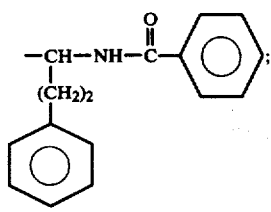

R₂ is methyl; and R₃ and R₆ are an alkali metal salt.

9. The compound of claim 6 wherein R₁ is

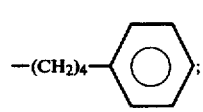

R₂ is methyl; R₃ is ethyl; and R₆ is an alkali metal salt.

10. The compound of claim 6 wherein R₁ is

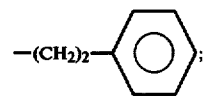

R₂ is methyl; and R₃ and R₆ are an alkali metal salt.

11. The compound of claim 6 wherein R₁ is

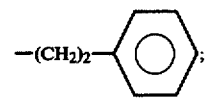

R₂ is methyl; R₃ is

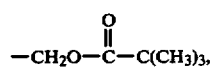

and R₆ is an alkali metal salt.

12. The compound of claim 6 wherein R₁ is

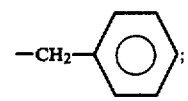

R₂ is methyl; and R₃ and R₆ are an alkali metal salt.

13. The compound of claim 6 wherein R₁ is

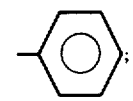

R₂ is methyl; and R₃ and R₆ are an alkali metal salt.

14. The compound of claim 6 wherein R₁ is

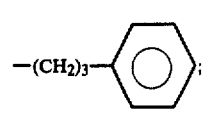

R₂ is methyl; and R₃ and R₆ are an alkali metal salt.

15. The compound of claim 6 wherein R₁ is

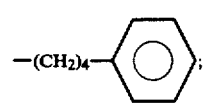

R₂ is hydrogen; and R₃ and R₆ are an alkali metal salt.

16. The compound of claim 6 wherein R₁ is

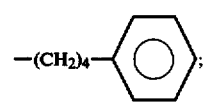

R₂ is hydrogen; and R₃ and R₆ are an alkali metal salt.

17. The compound of claim 1 wherein X is

18. The compound of claim 1 wherein $R_1$ is

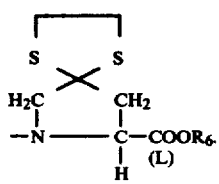

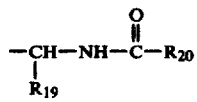

and $R_{19}$ and $R_{20}$ are independently selected from lower alkyl of 1 to 4 carbons or

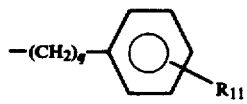

wherein q is zero or an integer from 1 to 4 and $R_{11}$ is hydrogen, methyl, methoxy, methylthio, chloro, bromo, fluoro, or hydroxy.

19. A compound of claim 18 wherein X is

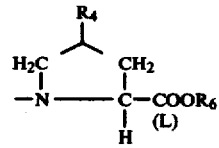

and $R_4$ is hydrogen.

20. A composition useful for treating hypertension comprising a pharmaceutically acceptable carrier and a hypotensive compound or pharmaceutically acceptable salt thereof defined in claim 1.

21. The method of alleviating hypertension in a mammalian specie which comprises administering an effective amount of the composition of claim 20.

* * * * *